US010485881B2

(12) United States Patent
Bradbury et al.

(10) Patent No.: US 10,485,881 B2
(45) Date of Patent: *Nov. 26, 2019

(54) NANOPARTICLE DRUG CONJUGATES

(71) Applicants: Memorial Sloan Kettering Cancer Center, New York, NY (US); Cornell University, Ithaca, NY (US)

(72) Inventors: Michelle S. Bradbury, New York, NY (US); Barney Yoo, New York, NY (US); Ulrich Wiesner, Ithaca, NY (US); Kai Ma, Ithaca, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/137,709

(22) Filed: Sep. 21, 2018

(65) Prior Publication Data
US 2019/0070310 A1    Mar. 7, 2019

Related U.S. Application Data

(63) Continuation of application No. 14/722,307, filed on May 27, 2015, now Pat. No. 10,111,963.
(Continued)

(51) Int. Cl.
*A61K 9/00* (2006.01)
*A61K 47/69* (2017.01)
(Continued)

(52) U.S. Cl.
CPC ........ *A61K 47/6923* (2017.08); *A61K 31/506* (2013.01); *A61K 31/5377* (2013.01);
(Continued)

(58) Field of Classification Search
CPC .................................................. A61K 47/6923
See application file for complete search history.

(56) References Cited

U.S. PATENT DOCUMENTS 3,867,519 A    2/1975 Michaels
3,870,791 A    3/1975 Haddad et al.
(Continued)

FOREIGN PATENT DOCUMENTS

WO    WO-99/22026 A1    5/1999
WO    WO-2004/074504 A2    9/2004
(Continued)

OTHER PUBLICATIONS

Ballou, B. et al., Sentinel Lymph Node Imaging Using Quantum Dots in Mouse Tumor Models, Bioconjugate Chem. 18:389-396 (2007).
(Continued)

*Primary Examiner* — Paul W Dickinson
(74) *Attorney, Agent, or Firm* — Choate, Hall & Stewart LLP; William R. Haulbrook; Margo R. Monroe

(57) ABSTRACT

Described herein are nanoparticle drug conjugates (NDCs), which, in certain embodiments, comprise a non-toxic, multi-modality, clinically proven silica-based nanoparticle platform with covalently attached drug molecules/moieties. The nanoparticle drug conjugates (NDCs) demonstrate imaging capability and targeting ligands which efficiently clear through the kidneys. Furthermore, the conjugates incorporate therapeutic agents for cancer detection, prevention, and/or treatment.

24 Claims, 19 Drawing Sheets

Related U.S. Application Data

(60) Provisional application No. 62/004,738, filed on May 29, 2014, provisional application No. 62/094,923, filed on Dec. 19, 2014.

(51) Int. Cl.
*A61K 31/506* (2006.01)
*A61K 31/5377* (2006.01)
*A61K 47/65* (2017.01)
*A61K 47/60* (2017.01)
*A61K 49/00* (2006.01)
*A61K 51/12* (2006.01)

(52) U.S. Cl.
CPC .............. *A61K 47/60* (2017.08); *A61K 47/65* (2017.08); *A61K 49/0093* (2013.01); *A61K 51/1244* (2013.01)

(56) References Cited

U.S. PATENT DOCUMENTS

| | | | |
|---|---|---|---|
| 4,051,842 A | 10/1977 | Hazel et al. |
| 4,136,177 A | 1/1979 | Lin et al. |
| 4,140,122 A | 2/1979 | Kuhl et al. |
| 4,255,415 A | 3/1981 | Chrai et al. |
| 4,383,529 A | 5/1983 | Webster |
| 4,688,506 A | 8/1987 | van Breems |
| 4,713,224 A | 12/1987 | Tamhankar et al. |
| 4,774,339 A | 9/1988 | Haugland et al. |
| 4,788,603 A | 11/1988 | Fujimura et al. |
| 4,810,636 A | 3/1989 | Corey |
| 4,812,409 A | 3/1989 | Babb et al. |
| 4,931,279 A | 6/1990 | Bawa et al. |
| 5,187,288 A | 2/1993 | Kang et al. |
| 5,248,782 A | 9/1993 | Haugland et al. |
| 5,274,113 A | 12/1993 | Kang et al. |
| 5,433,896 A | 7/1995 | Kang et al. |
| 5,776,427 A | 7/1998 | Thorpe et al. |
| 5,830,912 A | 11/1998 | Gee et al. |
| 6,254,852 B1 | 7/2001 | Glajch et al. |
| 6,268,222 B1 | 7/2001 | Chandler et al. |
| 7,601,355 B2 | 10/2009 | Howard et al. |
| 8,084,001 B2 | 12/2011 | Burns et al. |
| 8,239,007 B2 | 8/2012 | Voegele et al. |
| 8,298,677 B2 | 10/2012 | Wiesner et al. |
| 8,389,679 B2 | 3/2013 | Eckert et al. |
| 8,409,876 B2 | 4/2013 | Wiesner et al. |
| 10,111,963 B2 | 10/2018 | Yoo et al. |
| 2003/0219785 A1 | 11/2003 | Hallahan et al. |
| 2004/0101822 A1 | 5/2004 | Wiesner et al. |
| 2004/0248856 A1 | 12/2004 | Lanza et al. |
| 2006/0106306 A1 | 5/2006 | Essner et al. |
| 2006/0173362 A1 | 8/2006 | Toms et al. |
| 2006/0183246 A1 | 8/2006 | Wiesner et al. |
| 2006/0245971 A1 | 11/2006 | Burns et al. |
| 2006/0251726 A1 | 11/2006 | Lin et al. |
| 2008/0097225 A1 | 4/2008 | Tearney et al. |
| 2008/0139787 A1 | 6/2008 | De Jesus et al. |
| 2008/0213377 A1 | 9/2008 | Bhatia et al. |
| 2008/0292556 A1 | 11/2008 | Texier-Nogues et al. |
| 2010/0261208 A1 | 10/2010 | Schollhorn |
| 2010/0262017 A1 | 10/2010 | Frangioni |
| 2011/0028662 A1 | 2/2011 | Wiesner et al. |
| 2013/0039848 A1 | 2/2013 | Bradbury et al. |
| 2014/0248210 A1 | 9/2014 | Bradbury et al. |
| 2015/0174268 A1* | 6/2015 | Li ........................ A61K 39/39 424/178.1 |
| 2015/0343091 A1 | 12/2015 | Yoo et al. |
| 2016/0202185 A1 | 7/2016 | Zhuang et al. |
| 2017/0239378 A1 | 8/2017 | Bradbury et al. |
| 2018/0169264 A1 | 6/2018 | Bradbury et al. |
| 2018/0326103 A1 | 11/2018 | Bradbury et al. |

FOREIGN PATENT DOCUMENTS

| | | |
|---|---|---|
| WO | WO-2004/108902 A2 | 12/2004 |
| WO | WO-2006/099445 A2 | 9/2006 |
| WO | WO-2007/002540 A2 | 1/2007 |
| WO | WO-2007/136413 A2 | 11/2007 |
| WO | WO-2007/149062 A2 | 12/2007 |
| WO | WO-2008/044138 A1 | 4/2008 |
| WO | WO-2008/142571 A2 | 11/2008 |
| WO | WO-2009/029870 A2 | 3/2009 |
| WO | WO-2009/064964 A2 | 5/2009 |
| WO | WO-2011/003109 A1 | 1/2011 |
| WO | WO-2011/084620 A1 | 7/2011 |
| WO | WO-2011/130598 A1 | 10/2011 |
| WO | WO-2013/192609 A1 | 12/2013 |
| WO | WO-2014/011973 A2 | 1/2014 |
| WO | WO-2018/237253 A1 | 12/2018 |

OTHER PUBLICATIONS

Benezra, M. et al., Targeted multimodal silica nanoparticles with efficient urinary excretion for nanomedicine, Cancer Research, 64(7), one page (2009).

Bogush, G. H. et al., Preparation of Monodisperse Silica Particles: Control of Size and Mass Fraction, J. Non-Cryst. Solids, 104:95-106 (1988).

Brien, J. F. et al., A Study of the Calcium Carbimide-Ethanol Interaction in Man, Europ. J. Clin. Pharmacol. 14(2):133-41 (1978).

Brülisauer, L. et al., Disulfide-containing parenteral delivery systems and their redox-biological fate, Journal of Controlled Release, 195:147-154 (2014).

Burns, et al., Fluorescent Silica Nanoparticles with Efficient Urinary Excretion for Nanomedicine, Nano Letters 9(1):442-8 (2009).

Chakraborty, M. et al., External Beam Radiation of Tumors Alters Phenotype of Tumor Cells to Render Them Susceptible to Vaccine-Mediated T-Cell Killing, Cancer Research, 64:4328-4337 (2004).

Cho, Y. S. et al., Cetuximab-conjugated magneto-fluorescent silica nanoparticles for in vivo colon cancer targeting and imaging, Cancer Letters, 299:63-71 (2010).

Crespi, M. D. et al., Mitroxantrone Affects Topoisomerase Activities in Human Breast Cancer Cells, Biochemical and Biophysical Research Communications, 136(2):521-8 (1986).

Cressman, S. et al., Binding and Uptake of RGD-Containing Ligands to Cellular $\alpha_v\beta_3$ Integrins, Int J Pept Res Ther, 15:49-59 (2009).

Cristy, M. and Eckerman, K. F., Specific absorbed fractions of energy at various ages from internal photon sources (I-VII). Oak Ridge National Laboratory Report ORNL/TM-8381N1-7. Springfield, VA: National Technical Information Service, Dept. of Commerce (1987).

Crow, R. T. and Crothers, D. M., Inhibition of Topoisomerase I by Anthracycline Antibiotics: Evidence for General Inhibition of Topoisomerase I by DNA-Binding Agents, J. Med. Chem. 37(19):3191-3194 (1994).

De Jong, M. et al., Comparison of $^{111}$In-Labeled Somatostatin Analogues for Tumor Scintigraphy and Radionuclide Therapy, Cancer Res., 58:437-41 (1998).

De Jong, M. et al., Internalization of radiolabelled [DTPA$^0$]octreotide and [DOTA0,Tyr$^3$]ocetreotide:peptides for somatostatin receptor-targeted scintigraphy and radionuclide therapy, Nucl. Med. Commun., 19(3):283-288 (1998).

Denny, W. A. and Baguley, B. C., Dual Topoisomerase I/II Inhibitors in Cancer Therapy, Curr. Top. Med. Chem., 3(3):339-353 (2003).

Detappe, A. et al., Advanced multimodal nanoparticles delay tumor progression with clinical radiation therapy, Journal of Controlled Release, 238:103-113 (2016).

Ding, Y. et al., The performance of thiol-terminated PEG-paclitaxel-conjugated gold nanoparticles, Biomaterials, 34:10217-10227 (2013).

Doronina, S. O. et al., Novel Peptide Linkers for Highly Potent Antibody Auristatin Conjugate, Bioconjugate Chem., 19(10):1960-1963, (2008).

(56) References Cited

OTHER PUBLICATIONS

Etrych, T. et al., Biodegradable start HPMA polymer-drug conjugates: Biodegradability, distribution and anti-tumor efficacy, Journal of Controlled Release, 154:241-248 (2011).
Foglesong, P. D. et al., Doxorubicin inhibits human DNA topoisomerase I, Cancer Chemother. Pharmacol., 30(2):123-125 (1992).
Frauwirth, K. A. and Thompson, C. B., Activation and inhibition of lymphocytes by costimulation, The Journal of clinical Investigation, 109(3):295-299 (2002).
Fuller, J. E. et al., Intracellular delivery of core-shell fluorescent silica nanoparticles, Science Direct, Biomaterials, 29:1526-1532 (2008).
Gatto, B. et al., Identification of Topoisomerase I as the Cytotoxic Target of the Protoberberine Alkaloid Coralyne, Cancer Res., 15(12):2795-2800 (1996).
Gladson, C. A. and Cheresh, D. A., Glioblastoma Expression of Vitronectin and Alpha v Beta 3 Integrin, Adhesion Mechanism for Transformed Glial Cells, J. Clin. Invest. 88:1924-1932 (1991).
Herz, E. et al., Large Stokes-Shift Fluorescent Silica Nanoparticles with Enhanced Emission over Free Dye for Single Excitation Multiplexing, Macromol Rapid Commun., 30(22):1907-1910 (2009).
Hilderbrand, S. A. and Weissleder, R., Near-infrared fluorescence: application to in vivo molecular imaging, Curr. Opin. Chem. Bioi., 14:71-9 (2010).
International Search Report, PCT/US2010/040994, dated Aug. 30, 2010.
International Search Report, PCT/US2015/032565, 4 pages, dated Aug. 21, 2015.
Kalbasi, A. et al., Radiation and immunotherapy: a synergistic combination, Clinical review, The Journal of Clinical Investigation, 127(7):2756-2763 (2013).
Kim, S. et al., Near-infrared fluorescent type II quantum dots for sentinel lymph node mapping, Nature Biotechnology 22(1):93-97 (2004).
Kim, Y. H. et al., In situ vaccination against mycosis fungoides by intratumoral injection of a TLR9 agonist combined with radiation: a phase 1/2 study, Blood, 119(2):355-363 (2012).
Koole et al., Paramagnetic lipid-coated silica nanoparticles with a fluorescent quantum dot core: a new contrast agent platform for multimodality imaging, Bioconjugate Chem., 19(12):2471-2479 (2008).
Krenning, E. P. et al, Somatostatin Receptor Scintigraphy with Indium-111-DTPA-D-Phe-1-Octreolide in Man: Metabolism, Dosimetry and Comparison with Iodine-123-Tyr-3-Octreotide, J Nucl. Med. 33:652-8 (1992).
Larson, D. R. et al., Silica Nanoparticle Architecture Determines Radiative Properties of Encapsulated Fluorophores, Chem. Mater. 20:2677-2684 (2008).
Lewis et al. Comparison of Four 64Cu-labeled Somatostatin Analogs in Vitro and in a Tumor-Bearing Rat Model: Evaluation of New Derivatives for Positron Emission Imaging and Targeted Radiotherapy. J Med Chem., 42:1341-7 (1999).
Li, T. et al., Human Topoisomerase I Poisoning by Protoberberines: Potential Roles for Both Drug-DNA and Drug-Enzyme Interactions, Biochemistry, 39(24):7107-7116 (2000).
Li, Z. et al., $^{64}$Cu-labeled Tetrameric and Octomeric RGD Peptides for Small-Animal PET of Tumor $\alpha_v$ $\beta_3$ Integrin Expression, J. Nucl Med. 48:1162-1171 (2007).
Loir, B. et al., Expression of the MC1 Receptor Gene in Normal and Malignant Human Melanocytes. A Semiquantitative RT-PCR Study, Cell Mol. Biol., 45(7):1083-1092 (1999).
Makhey et al., Sbustitute Benzo[i]phenanthridines as Mammalian Topoisomerase-Targeting Agents, Bioorg. Med. Chem. 11(8):1809-1820 (2003).
McKeage et al., Phase I and Pharmacokinetic Study of an Oral Platinum Complex Given Daily for 5 Days in Patients With Cancer, Journal of Clinical Oncology, 15(7):2691-2700 (1997).
Montet, X. et al., Multivalent Effects of RGD Peptides Obtained by Nanoparticle Display, J. Med. Chem. 49:6087-6093 (2006).
Ohnishi, S. et al., Organic Alternatives to Quantum Dots for Intraoperative Near-Infrared Fluorescent Sentinel Lymph Node Mapping, Molecular Imaging 4(3):172-181 (2005).
Ow, H. et al., Bright and Stable Core-Shell Fluorescent Silica Nanoparticles, Nano Letters, 5(1):113-117 (2005).
Papamicheal, D., The Use of Thymidylate Synthase Inhibitors in the Treatment of Advanced Colorectal Cancer: Current Status, The Oncologist, 4:478-487 (1999).
Patel, K. N. et al., MUC1 plays a role in tumor maintenance in aggressive thryroid carcinomas, Surgery 138(6):994-1002 (2005).
Piatyszek, M.A. et al., Iodo-Gen-Mediated Radioiodination of Nucleic Acids, J. Anal. Biochem. 172(2):356-359 (1988).
Pommier, Y., Topoisomerase I inhibitors: camptothecins and beyond, Nat. Rev. Cancer, 6(10):789-802 (2006).
Ren, G. et al., PET of Malignant Melanoma Using $^{18}$F-Labeled Metallopeptides, The Journal of Nuclear Medicine, 50(11):1865-1872 (2009).
Reubi, J.C. et al., Distribution of Somatostatin Receptors in Normal and Tumor Tissue, Metabolism, 39(9)(2):78-81 (1990).
Reubi, J.C. et al., Somatostatin Receptors and Their Subtypes in Human Tumors and in Peritumoral Vessels, Metabolism, 45(8)(1):39-41 (1996).
Rianasari, I. et al., Covalent Coupling of Nanoparticles with Low-Density Functional Ligands to Surface via Click Chemistry, Int. J. Mol. Sci. 14:3705-3717 (2013).
Ruoslahti, E. and Pierschbacher, M. D., New Perspectives in Cell Adhesion: RGD and Integrins, Science 238:491 (1987).
Sadasivan, et al., Alcoholic Solvent Effect on Silica Synthesis—NMR and DLS Investigation, J. Sol-Gel Science and Technology, 12:5-14 (1998).
Sanderson, R. J. et al., In vivo Drug-Linker Stability of an Anti-CD30 Dipeptide-Linked Auristatin Immunoconjugate, Clinical cancer Research, 11:843-852 (2005).
Seftor, R. E. B. et al., Role of the alpha v beta 3 integrin in human melanoma cell invasion, Proc. Natl. Acad. Sci., 89:1557-1561 (1992).
Seung, S. K. et al., Phase 1 Study of Stereotactic Body Radiotherapy and Interleukin-2: Tumor and Immunological Responses, Science Trnslational Medicine 14(137):137ra74 1-7 (2012).
Seymour, L.W., Passive Tumor Targeting of Soluble Macromolecules and Drug Conjugates, Critical Reviews in Therapeutic Drug Carrier Systems, 9(2):135-187 (1992).
Sharma, P. et al, Nanoparticles for bioimaging, Advances in Colloid and Interface Science, 123-126:471-485 (2006).
Slowing, I. I. et al., Mesoporous silica nanoparticles as controlled release drug delivery and gene transfection carriers, Advanced Drug Delivery Reviews, 60:1278-1288 (2008).
Soster, M. et al., Targeted dual-color silica nanoparticles provide univocal identification of micrometastases in preclinical models of colorectal cancer, International Journal of Nanomedicine, 7:4797-4807 (2012).
Stabin, M. G. et al., OLINDA/EXM: The Second-Generation Personal Computer Software for Internal Dose Assessment in Nuclear Medicine, J Nucl Med. 46:1023-1027 (2005).
Takeshima, T. et al., Local Radiation Therapy Inhibits Tumor Growth through the Generation of Tumor-Specific CTL: Its Potentiation by Combination with Th1 Cell Therapy, Cancer Research, 70(7):2697-2706 (2010).
Tanaka, E. et al, Image-Guided Oncologic Surgery Using Invisible Light: Completed Pre-Clinical Development for Sentinel Lymph Node Mapping, Annals of Surgical Oncology 13(12):1671-1681 (2006).
Thakor, A. S. and Gambhir, S. S., Nanooncology: The Future of Cancer Diagnosis and Therapy, CA Cancer J. Clin., 63(6):395-418 (2013).
Topalian, S. L. et al., Safety, Activity, and Immune Correlates of Anti-PD-1 Antibody in Cancer, The New England Journal of Medicine, 366(26):2443-2454 (2012).
Van Schooneveld, M. M. et al., Improved Biocompatibility and Pharmacokinetics of Silica Nanoparticles by Means of a Lipid Coating: A Multimodality Investigation, Nano Letters, 8(8):2517-2525 (2008).

(56) References Cited

OTHER PUBLICATIONS

Vejayakumaran, P. et al., Structural and thermal characterizations of silica nanoparticles grafted with pendant maleimide and epoxide grops, Journal of Colloid and Interface Science, 328:81-91 (2008).
Wang, X. et al., Folate Receptor-Targeted Aggregation-Enhanced Near-IR Emitting Silica Nanoprobe for One-Photon in Vivo and Two-Photon ex Vivo FLuorescence Bioimaging, Bioconjugate Chemistry, 22:1438-1450 (2011).
Wang, Y. et al., Tumor cell targeted delivery by specific peptide-modified mesoporous silica nanoparticles, J. Mater. Chem., 22:14608-14616, (2012).
Webb, et al., Sphingomyelin-cholesterol liposomes significantly enhance the pharmacokinetic and therapeutic properties of vincristine in murine and human tumour models, British J. of Cancer 72:896-904 (1995).
Webster, A. et al., Optical calcium sensors: development of a generic method for their introduction to the cell using conjugated cell penetrating peptides, Analyst, 130:163-70 (2005).
Wersäll, P.J. et al., Regression of non-irradiated metastases after extracranial stereotactic radiotherapy in metastatic renal cell carcinoma, Acta Oncologica, 45:493-497 (2006).
Written Opinion, PCT/US2010/040994, dated Aug. 30, 2010.
Written Opinion, PCT/US2015/032565, 6 pages, dated Aug. 21, 2015.
Wu, P. et al., Imaging Breast Cancer Cells and Tissues Using Peptide-Labeled Fluorescent Silica Nanoparticles, Journal of Nanoscience and Nanotechnology, 8(5):2483-2487 (2008).
Xu, Z. et al., DNA Minor Groove Biding-Directed Poisoning of Human DNA Topoisomerase I by Terbenzimidazoles, Biochemistry 37(10):3558-3566 (1998).
Zeng, J. et al., Anti-PD-1 Blockade and Stereotactic Radiation Produce Long-Term Survival in Mice With Intracranial Gliomas, Intl. J. Radiation Oncol. Biol. Phys., 86(2):343-349 (2013).
Zhong, Y. J. et al., Cathepsin B-cleavable doxorubicin prodrugs for targeted cancer therapy (Review), International Journal of Oncology, 42:373-383, (2013).
Benezra, M. et al., Multimodal silica nanoparticles are effective cancer-targeted probes in a model of human melanoma, Journal of Clinical Investigation, 121(7):2768-2780 (2011).
Benezra, M. et al., Ultrasmall Integrin-Targeted Silica Nanoparticles Modulate Signaling Events and Cellular Processes in a Concentration-Dependent Manner, Small, 11(14):1721-1732 (2015).
Dixon, S. J. et al., Ferroptosis: An Iron-Dependent Form of Nonapoptotic Cell Death, Cell, 149(51):1060-1072 (2012).
Kim, D. et al., Antitumor activity of sorafenib-incorporated nanoparticles of dextran/poly (dl-lactide-co-glycolide) block copolymer, Nanoscale Research Letters, 7(1):91 (2012).
Kim, S. E. et al., Ultrasmall nanoparticles induce ferroptosis in nutrient-deprived cancer cells and suppress tumour growth, Nature Nanotechnology, 11(11):977-985, (2016).
Lachaier, E. et al., Sorafenib Induces Ferroptosis in Human Cancer Cell Lines Originating from Different Solid Tumors, Anticancer Research, 34:6417-6422 (2014).
Mayer, R. J. et al., Randomized Trial of TAS-102 for Refractory Metastatic Colorectal Cancer, NEJM, 372(20):1909-1919 (2015).
Phillips, E. et al., Clinical translation of an ultrasmall inorganic optical-PET imaging nanoparticle probe, Science Translational Medicine, 6(260):260ra149-260ra149 (2014).
Tavernaro, I. et al., Bright Fluorescent silica-nanoparticle probes for high-resolution STED and confocal microscopy, Beilstein Journal of Nanotechnology, 8:1283-1296, (2017).
Zhang, X. L. et al., Ultrasmall 1-6, radioiodinated alpha MSH-C dots for melanoma imaging and therapy, Journal of Labelled Compounds and Radiopharmeceuticals, 58(1):5114 (2015).
Lee. G. Y. et al., Theranostic Nanoparticles with Controlled Release of Gemcitabine for Targeted Therapy and MRI of Pancreatic Cancer, ACS NANO, 7(3):2078-2089, (2013).

\* cited by examiner

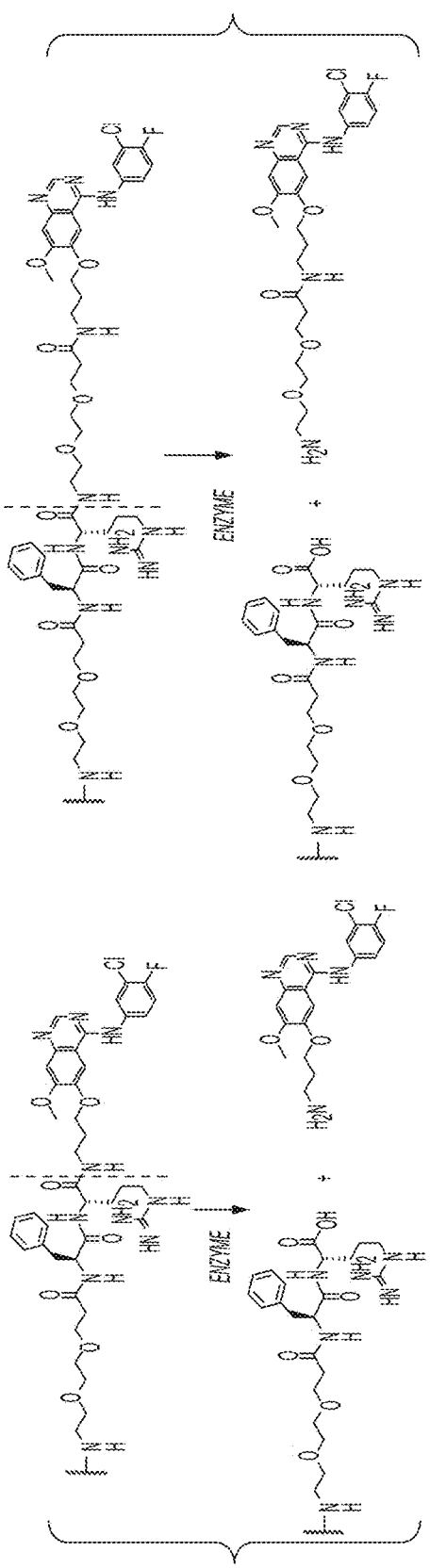
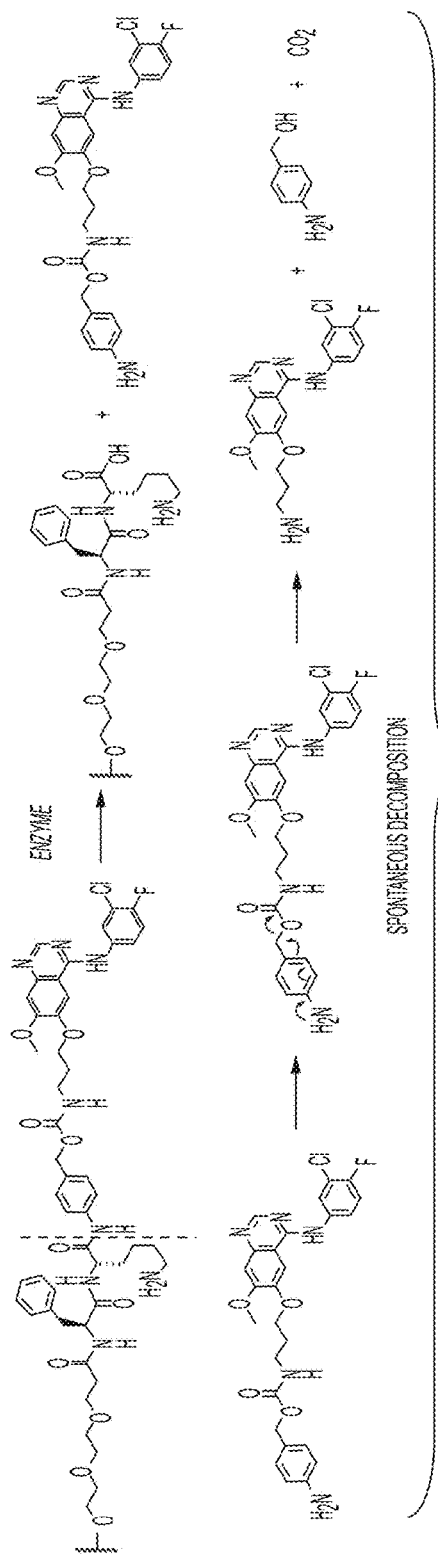
FIG. 2A
FIG. 2B
FIG. 2C

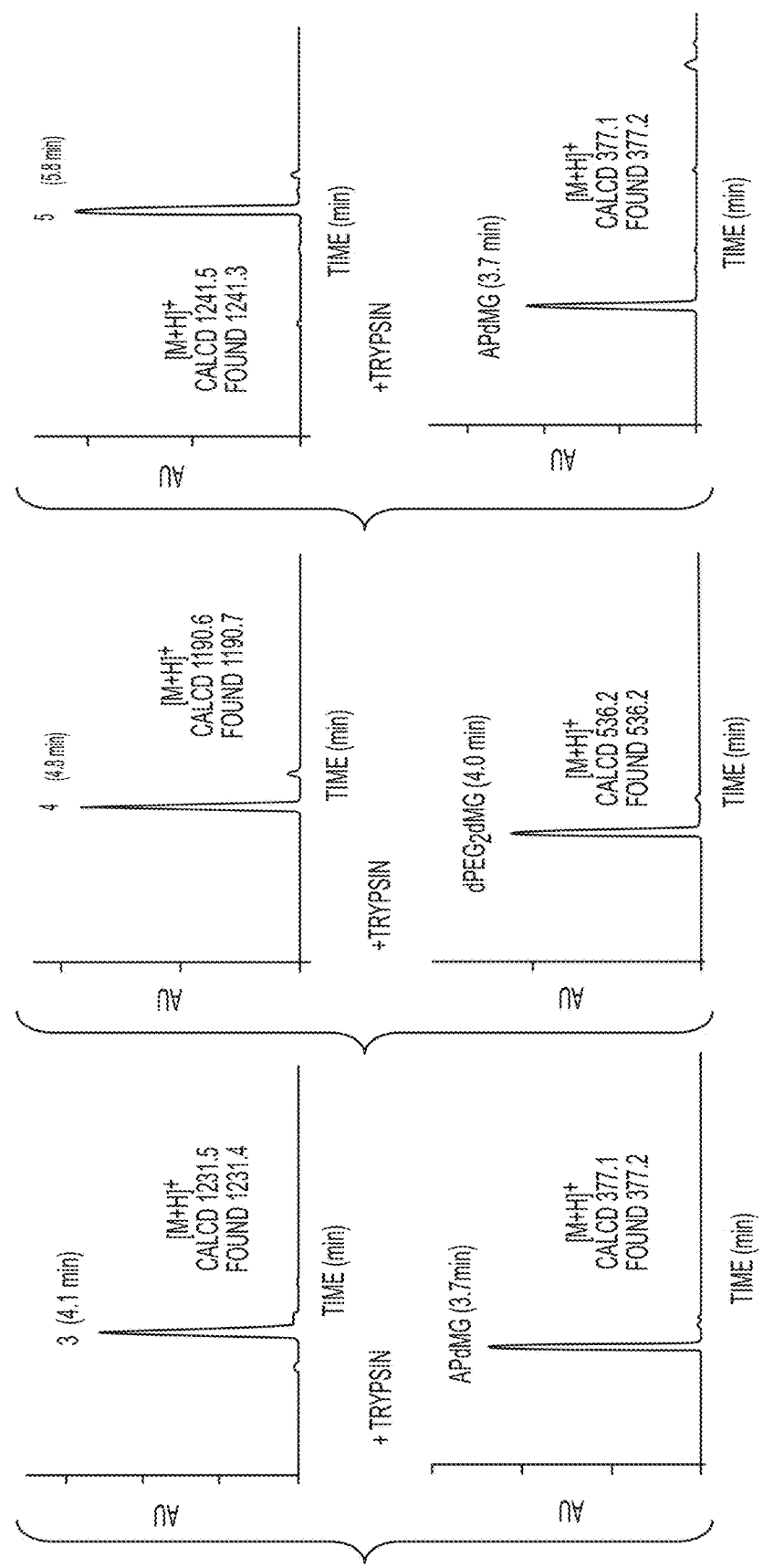

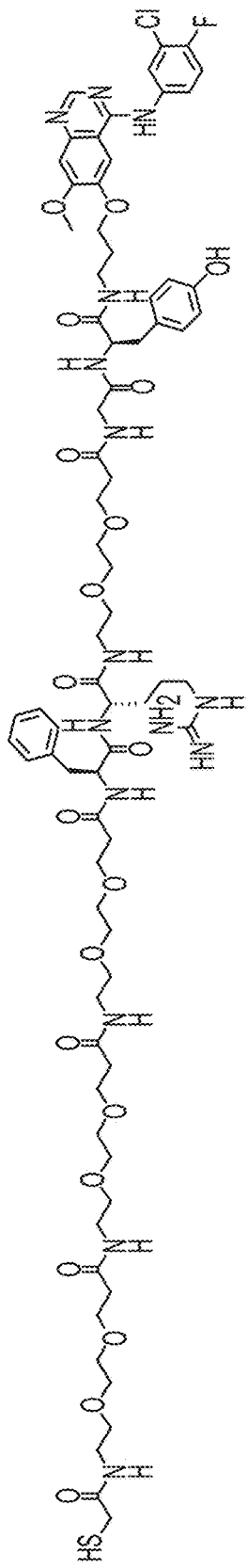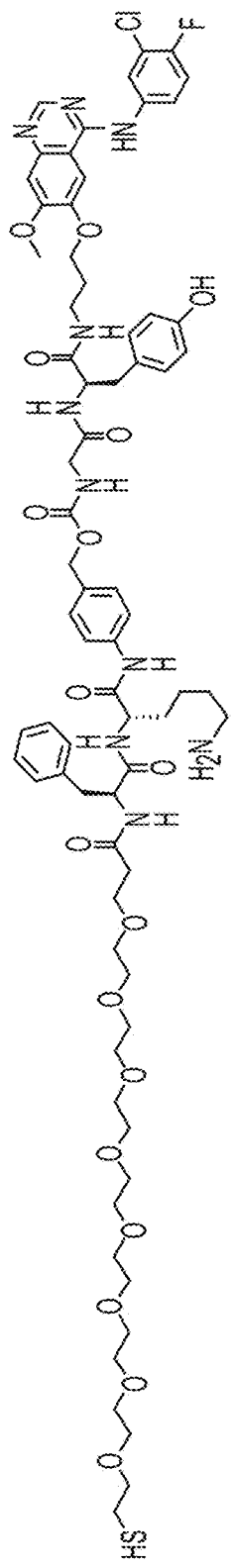
FIG. 9A
FIG. 9B

SCHEME 2

SCHEME 5

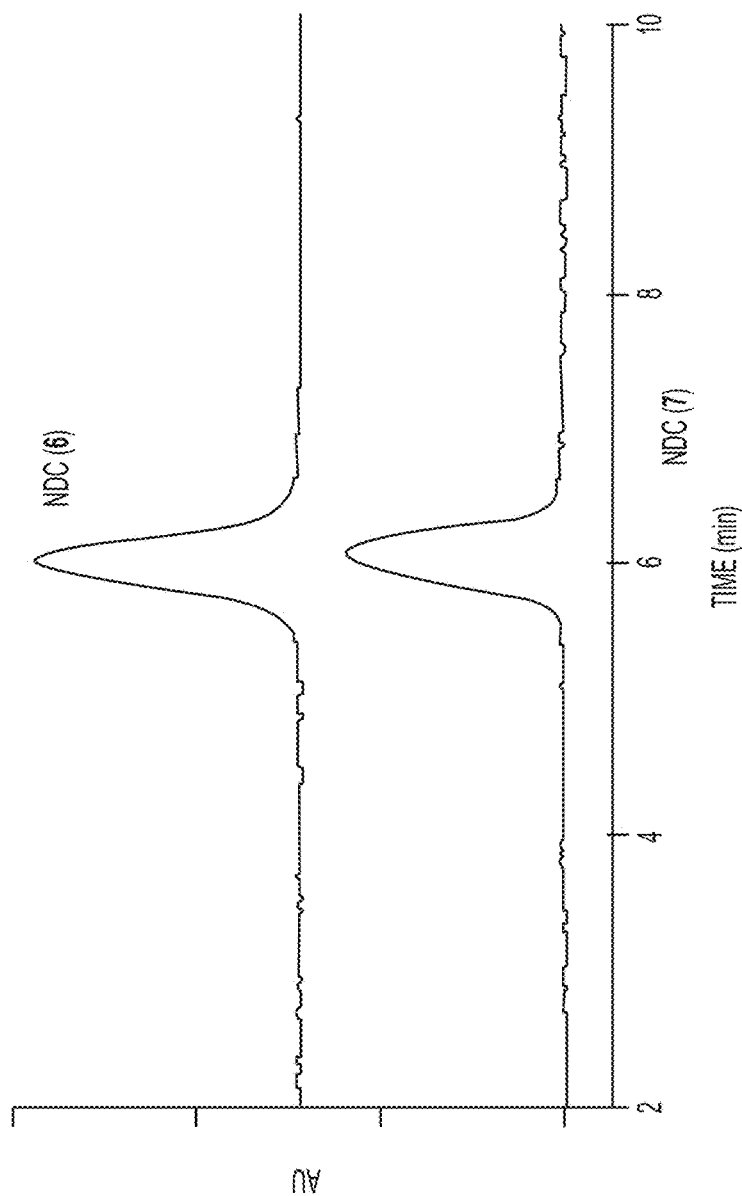

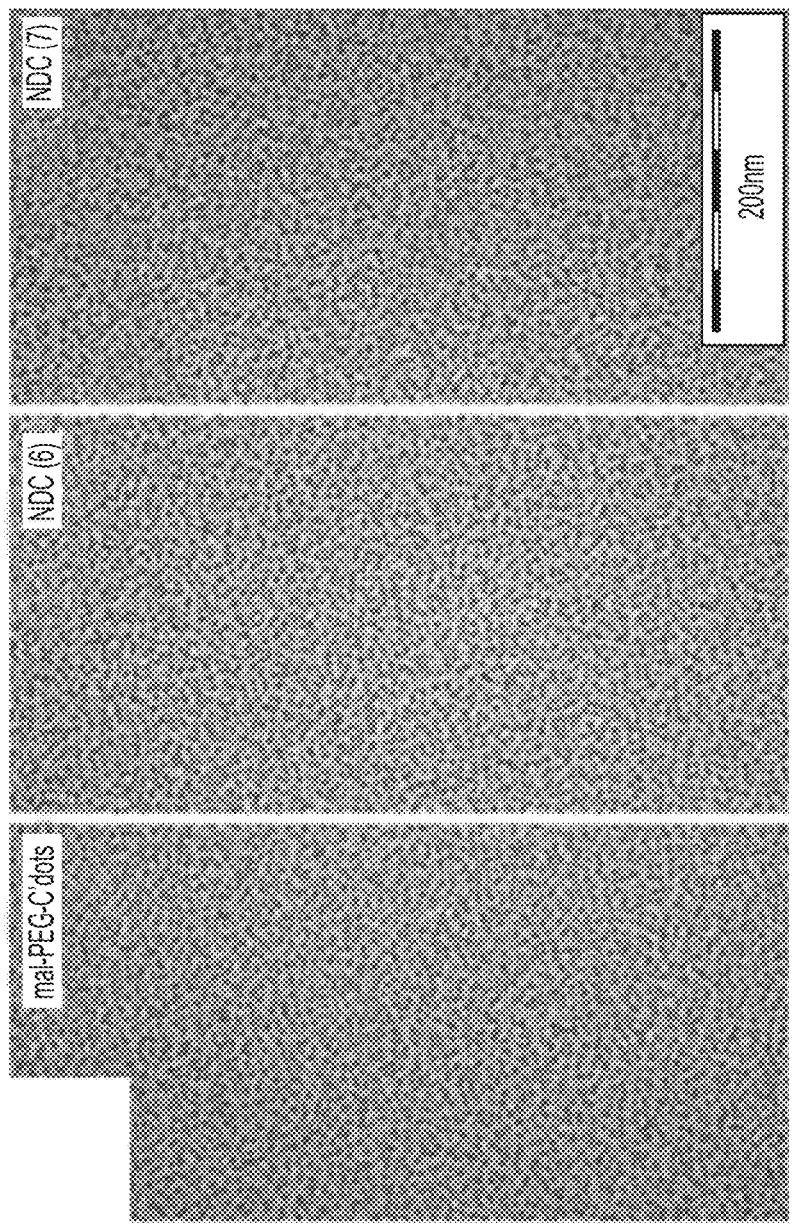

NANOPARTICLE DRUG CONJUGATES

CROSS-REFERENCE TO RELATED APPLICATIONS

This application claims priority to and the benefit of, and incorporates herein by reference in their entireties, U.S. Provisional Patent Application Nos. 62/004,738 and 62/094,923, filed May 29, 2014 and Dec. 19, 2014, respectively.

FIELD OF THE INVENTION

This invention relates generally to nanoparticle conjugates for delivery of therapeutic agents (e.g., targeted drug release) for the detection, prevention, and treatment of cancer and other diseases.

BACKGROUND OF THE INVENTION

Nanotherapeutic delivery vehicles are typically macro- or supra-molecular multicomponent systems, ranging in size from 1-1,000 nm, that are either inherently therapeutic (e.g., no active pharmaceutical ingredient) or function as therapeutic delivery systems. To date, liposomal nanoparticles and biologics comprise a large proportion of the number of FDA-approved products or products in clinical trials used to treat a variety of cancer types, while a number of polymer-based particle formulations are currently in early phase trials.

Desirable candidates for nanotherapeutic delivery systems share a common feature of incorporating and releasing a drug compound in a controlled manner, which can favorably alter drug bioavailability and pharmacokinetics, while minimizing off-target toxicities. Ideally, an imaging label is incorporated therein to assess their precise localization and retention at disease sites.

However, these systems function using different mechanisms. For example, antibody drug conjugates (ADCs) achieve lower drug toxicity primarily through active targeting of tumor cells and conditional release of drug molecules. Upon binding a cell surface antigen, active drug release occurs after cellular internalization and endosomal uptake. On the other hand, liposomes and polymer-based drug delivery systems, which are typically much larger assembled complexes (~20-150 nm diameters) passively loaded with a greater payload (~10,000 drug molecules for Doxil), have generally lacked targeting capabilities (BIND-014 is an exception). Therefore, these complexes rely primarily on the well-known enhanced permeability and retention (EPR) effect for the successful delivery of nano-formulated drugs. While interstitial permeation of liposomes may be poor due to their size, the free drug is released through various mechanisms that are not entirely understood. For example, Abraxane (~140 nm) relies on a different approach to enhance the bioavailability of a hydrophobic compound. In this case, a specific formulation of albumin and drug (paclitaxel) forms the initial complex, which is in turn estimated to disperse into smaller protein-drug aggregates upon injection.

Thus, there is a need for a unique platform for drug delivery that provides adequate biostability and exhibits controlled release of the bioactive compound at a desired site.

SUMMARY OF THE INVENTION

Presented herein are methods and compositions of nanoparticle drug conjugates (NDC), specifically silica-based nanoparticle platform with covalently attached drug molecules. A NDC has been demonstrated as a nanotherapeutic. The combination of size, molecular composition and chemistry (e.g., mode of drug release) may leverage the beneficial properties seen in other nanotherapeutic products with the aim of overcoming key obstacles hampering traditional formulations, including narrow therapeutic indices, dose-limiting toxicities, and limited clinical utility.

In one aspect, the invention is directed to a nanoparticle drug conjugate (NDC) comprising: a nanoparticle (e.g., having a diameter within a range from 1 nm to 25 nm); a linker moiety; and a drug moiety (e.g., dasatinib or gefitinib, including any analog thereof), wherein the nanoparticle is coated with an organic polymer (e.g., wherein the organic polymer comprises at least one bifunctionalized maleimide silyl-polyethylene glycol group attached to at least one linker-drug construct), and wherein the drug moiety and linker moiety form a cleavable (e.g., via a protease) linker-drug construct that is covalently linked to the nanoparticle (e.g., via the linker moiety) (e.g., wherein the average drug moiety to nanoparticle ratio ranges from 1 to 20).

In certain embodiments, the linker moiety comprises one or more amino acids (e.g., a peptide or polypeptide) (e.g., from 1 to 10 amino acids). In certain embodiments, the linker moiety comprises (Amino-(spacer)$_x$)$_y$-peptide or (spacer)$_z$-peptide [e.g., dipeptide (e.g., phenylalanine-arginine (Phe-Arg) or phenylalanine-lysine (Phe-Lys))] wherein the spacer has from 2 to 50 atoms (e.g., wherein the spacer is PEG), wherein x is an integer from 1 to 5, wherein y is an integer from 1 to 5, wherein z is an integer from 5 to 15, and wherein the linker moiety comprises a degradable moiety (e.g., an amide bond) between the linker moiety and the drug moiety (e.g., allowing cleavage of the drug moiety in the presence of a protease). In certain embodiments, the linker moiety comprises a spacer (e.g., polyethylene glycol (PEG)), PEG$_2$, para-aminobenzyloxy carbamate (PABC)) between a peptide and the drug moiety. In certain embodiments, the NDCs further comprise a fluorescent compound (e.g., associated with the nanoparticle, e.g., within the core of the nanoparticle). In certain embodiments, the NDCs further comprise a radiolabel.

In certain embodiments, the linker moiety is capable of undergoing hydrolysis at the C-terminal end upon protease (e.g., serine protease (e.g., trypsin), cysteine protease (e.g., cathepsin B)) binding, thereby releasing the drug moiety from the nanoparticle.

In certain embodiments, the drug moiety comprises a receptor tyrosine kinase (RTK) inhibitor (e.g., dasatinib or gefitinib, including any analog thereof (e.g., any pharmaceutical and/or therapeutic equivalent thereof) modified to provide attachment to the linker moiety without perturbing underlying chemical structure of an active binding site of the drug moiety).

In certain embodiments, the NDCs further comprise from 1 to 20 targeting moieties (e.g., cyclic arginylglycylaspartic acid (cRGD)), wherein the targeting moieties bind to receptors on tumor cells.

In certain embodiments, the NDC is a theranostic.

In certain embodiments, the fluorescent compound is Cy5.5.

In certain embodiments, the drug moiety is attached to the radiolabel.

In certain embodiments, the nanoparticle further comprises a silica-based core and a silica shell surrounding at least a portion of the core.

Elements of embodiments described with respect to a given aspect of the invention may be used in various embodiments of another aspect of the invention. For example, it is contemplated that features of dependent claims depending from one independent claim can be used in apparatus and/or methods of any of the other independent claims.

BRIEF DESCRIPTION OF THE DRAWINGS

FIGS. 2A-2C show linker types.

FIG. 2A depicts that Phe-Arg-APdMG utilizes an amide bond for drug attachment. Enzymes recognize and bind the dipeptide sequence (Phe-Arg) then hydrolyze the amide bond C-terminal to the dipeptide and release APdMG 1.

FIG. 2B shows that Phe-Arg-dPEG$_2$APdMG uses dPEG$_2$APdMG 2, which incorporates a longer 10 atom PEG spacer between the drug and dipeptide to enhance drug release.

FIG. 2C shows that Phe-Lys-PABC-APdMG utilizes a para-aminobenzoxy-carbamate (or PABC) spacer group between the dipeptide (Phe-Lys) and aminopropyl-dMG. After enzyme catalyzed release of the spacer-drug, the spacer spontaneously decomposes from the drug.

FIGS. 3A-3C are representative enzyme (trypsin) catalyzed release of drug from linker-drug constructs. Data indicates that APdMG and dPEG$_2$APdMG are released from the constructs. Retention times are indicated in parenthesis. Trypsin assays were conducted at 37° C. in 10 mM phosphate buffer (pH 7.2)

FIG. 3A shows LCMS data of Phe-Arg-APdMG 3 (top) and Phe-Arg-APdMG+trypsin for 60 mins (bottom).

FIG. 3B shows LCMS data of Phe-Arg-dPEG$_2$-APdMG 4 (top) and Phe-Arg-dPEG$_2$-APdMG+trypsin for 10 mins (bottom).

FIG. 3C shows LCMS data of Phe-Arg-PABC-APdMG 5 (top) and Phe-Arg-PABC-APdMG+trypsin for 10 mins (bottom).

FIG. 4A depicts free linker-drug constructs treated with trypsin. Trypsin assays were conducted in 10 mM phosphate buffer (pH 7.2) at 37° C.

FIG. 4B depicts free linker-drug construct treated with cathepsin B. Cathepsin B assays were conducted in 25 mM sodium acetate buffer (pH 5.0).

FIG. 5A shows HPLC profile of NDC 6
FIG. 5B shows HPLC profile of NDC 7.

FIG. 6A shows drug release of C'dot-(Cy5)-PEG-Phe-Arg-dPEG$_2$APdMG 6 treated with trypsin.

FIG. 6B shows drug release of C'dot-(Cy5)-PEG-Phe-Lys-PABC-APdM 7 treated with cathepsin B.

FIGS. 9A and 9B show linker-drug constructs, Phe-Arg-dPEG$_2$-D-Tyr-aminopropyl-dMG and Phe-Lys-PABC-D-Tyr-aminopropyl-dMG that incorporate a D-tyrosine residue with the drug component for attaching a radiolabel (compounds 23 and 24).

FIGS. 16A-16D shows characterization of mal-PEG-C' dots and NDC 6 and 7.

FIG. 16A shows analytical C18 reversed phase HPLC at 348 nm.

FIG. 16B shows a TEM image.

FIG. 16C shows absorbance and emission spectra.

FIG. 16D shows FCS correlation curves.

Figure 1A:
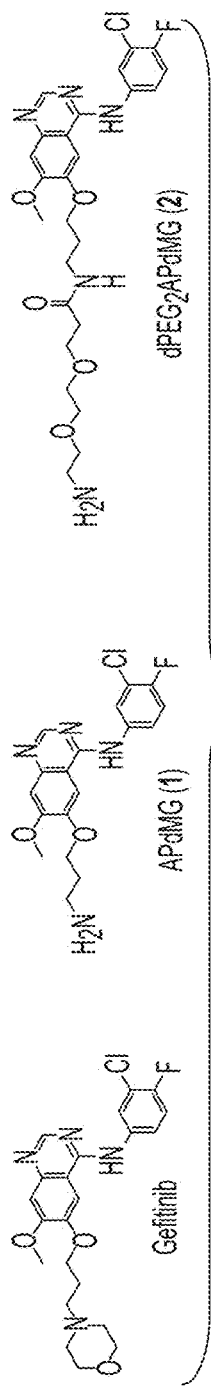
FIG. 1A depicts chemical structures of gefitinib and analogues (APdMG 1 and dPEG$_2$APdMG 2).

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising"

and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

The term "agent" refers to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or are not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized include small molecules, antibodies, antibody fragments, aptamers, siRNAs, shRNAs, DNA/RNA hybrids, antisense oligonucleotides, ribozymes, peptides, peptide mimetics, peptide nucleic acids, small molecules, etc. In some embodiments, an agent is or comprises a polymer. In some embodiments, an agent contains at least one polymeric moiety. In some embodiments, an agent comprises a therapeutic, diagnostic and/or drug.

The term "peptide" or "polypeptide" refers to a string of at least two (e.g., at least three) amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

As used herein, a "functional" biological molecule is a biological molecule in a form in which it exhibits a property and/or activity by which it is characterized. A biological molecule may have two functions (i.e., bifunctional) or many functions (i.e., multifunctional).

The term "in vitro" as used herein refers to events that occur in an artificial environment, e.g., in a test tube or reaction vessel, in cell culture, etc., rather than within a multi-cellular organism.

As used herein "in vivo" refers to events that occur within a multi-cellular organism, such as a human and a non-human animal. In the context of cell-based systems, the term may be used to refer to events that occur within a living cell (as opposed to, for example, in vitro systems).

The term "imaging agent" as used herein refers to any element, molecule, functional group, compound, fragments thereof or moiety that facilitates detection of an agent (e.g., a polysaccharide nanoparticle) to which it is joined. Examples of imaging agents include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available. Non-limiting fluorescent compounds that may be used in the present invention include, Cy5, Cy5.5 (also known as Cy5++), Cy2, fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red, LightCycler-Red 640, LightCycler Red 705, tetramethylrhodamine (TMR), rhodamine, rhodamine derivative (ROX), hexachlorofluorescein (HEX), rhodamine 6G (R6G), the rhodamine derivative JA133, Alexa Fluorescent Dyes (such as Alexa Fluor 488, Alexa Fluor 546, Alexa Fluor 633, Alexa Fluor 555, and Alexa Fluor 647), 4',6-diamidino-2-phenylindole (DAPI), Propidium iodide, AMCA, Spectrum Green, Spectrum Orange, Spectrum Aqua, Lissamine, and fluorescent transition metal complexes, such as europium.

As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

Described herein are nanoparticle drug conjugates (NDCs), which, in certain embodiments, comprise a non-toxic, multi-modality, clinically proven silica-based nanoparticle platform with covalently attached drug molecules/moieties. The nanoparticle drug conjugates (NDCs) demonstrate imaging capabilities and targeting ligands which efficiently clear through the kidneys. Furthermore, the conjugates incorporate therapeutic agents for cancer detection, prevention, and/or treatment. For example, NDCs containing specific receptor tyrosine kinase (RTK) inhibitors have been synthesized and are demonstrated to release drug compounds in a controlled and predictable manner. Furthermore, western blot analysis shows reduced RTK phosphorylation levels in cells, suggesting NDC based drug delivery in vitro.

In some embodiments, the silica-based nanoparticle platform comprises ultrasmall nanoparticles or "C dots," which are fluorescent, organo-silica core shell particles that have diameters controllable down to the sub-10 nm range with a range of modular functionalities. C dots are described by U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Incorporated into the silica matrix of the core are near-infrared dye molecules, such as Cy5.5, which provides its distinct optical properties. Surrounding the core is a layer or shell of silica. The silica surface is covalently modified with silyl-polyethylene glycol (PEG) groups to enhance stability in aqueous and biologically relevant conditions. These particles have been evaluated in vivo and exhibit excellent clearance properties owing largely to their size and inert surface. Among the additional functionalities incorporated into C dots are chemical sensing, non-optical (PET) image contrast and in vitro/in vivo targeting capabilities, which enable their use in visualizing lymph nodes for surgical applications, and melanoma detection in cancer.

C dots provide a unique platform for drug delivery due to their physical properties as well as demonstrated human in vivo characteristics. These particles are ultrasmall and benefit from EPR effects in tumor microenvironments, while retaining desired clearance and pharmacokinetic properties. To this end, described herein is a nanoparticle drug delivery system in which, in certain embodiments, drug constructs are covalently attached to C dots (or other nanoparticles). C dot-based NDCs for drug delivery provide good biostability, minimize premature drug release, and exhibit controlled release of the bioactive compound. In certain embodiments, peptide-based linkers are used for NDC applications. These linkers, in the context of antibodies and polymers, are stable both in vitro and in vivo, with highly predictable release kinetics that rely on enzyme catalyzed hydrolysis by lysosomal proteases. For example, cathepsin B, a highly expressed protease in lysosomes, can be utilized to facilitate drug release from macromolecules. By incorporating a short, protease sensitive peptide between the macromolecular backbone and the drug molecule, controlled release of the drug can be obtained in the presence of the enzyme.

In certain embodiments, the NDCs are ultrasmall (e.g., with average diameter from about 5 nm to about 10 nm, (e.g., about 6 nm)) and utilize enzyme sensitive linkers, for example, where drug release is catalyzed by proteases. In one example, gefitinib, an important epidermal growth factor receptor mutant (EGFRmt+)-tyrosine kinase inhibitor (TKI) cancer drug, was modified and incorporated onto the particles. The resulting NDCs exhibited excellent in vitro stability, solubility, and proved to be active in EGFRmt+-expressing NSCLC cells.

In certain embodiments, the NDCs comprise one or more targeting moieties, for example, to target a particular tissue type (e.g., a particular tumor). NDCs with target moieties enhance internalization of drugs in tumor cells (e.g., targeting ligands bind to receptors on tumor cells, and/or deliver drugs into tumor cells (e.g., by increased permeability)). For example, to create a particle therapeutic with an additional targeting moiety (e.g., cRGD), silica nanoparticles are added to a mixture of cRGDY-PEG conjugates and maleimide bifunctionalized PEGs. The maleimide bifunctionalized PEGs support the additional attachment of drug-linker conjugates to create a theranostic product.

In some embodiments, ultrasmall particles may be associated with PET labels and/or optical probes. Nanoparticles may be observed in vivo (e.g., via PET) to evaluate drug accumulation in a target site. For example, nanoparticles with PET labels (e.g., without drug substances) may be administered first. Then, by analyzing the in vivo PET images of the nanoparticles, drug (e.g., conjugated with nanoparticles) concentration and accumulation rate in the tumor may be estimated. The dose may be determined based on the obtained estimation to provide personalized medicine (e.g., tumor size rather than the patient's body weight). In some embodiments, a radiolabeled drug may be traced in vivo. A highly concentrated chemotherapy drug is potentially dangerous if it is not targeted. In some embodiments, nanoparticles with optical probes (e.g., fluorophore) may be used for intraoperative imaging (e.g., where surface of tissue/tumor is exposed) and/or biopsies of tumors.

The therapeutic agent and nanoparticle can be radiolabeled or optically labelled separately, allowing independent monitoring of the therapeutic agent and the nanoparticle. In one embodiment, radiofluorinated (i.e., $^{18}$F) dasatinib is coupled with PEG-3400 moieties attached to the nanoparticle via NHS ester linkages. Radiofluorine is crucial for being able to independently monitor time-dependent changes in the distribution and release of the drug from the radioiodinated C24I) fluorescent (Cy5) nanoparticle. In this way, the pro drug (dasatinib) and nanoparticle can be monitored. This permits optimization of the prodrug design compared with methods in the prior art where no dual-labeling approach is used. In another embodiment, radio-therapeutic iodine molecules (e.g., $^{131}$I), or other therapeutic gamma or alpha emitters, are conjugated with PEG via a maleimide functional group, where the therapeutic agent may not dissociate from the PEG in vivo.

NDCs are drug compounds covalently attached to C dot nanoparticles (or other nanoparticles) through a molecular linker. In certain embodiments, linkers incorporate peptide (e.g., dipeptide) sequences sensitive to trypsin (control enzyme) and/or cathepsin B, which is an enzyme found predominantly in the lysosomes of cells. Experiments involving two classes of linker chemistries are described herein for controlled drug release—one incorporating an amide bond between the linker and drug; and another utilizing a degradable moiety between the linker and drug. In some embodiments, the linkers are designed to release the drug from the nanoparticle (e.g., C dot) under particular conditions, for example, proteolytic hydrolysis.

Example drugs that can be used include RTK inhibitors, such as dasatinib and gefitinib, can target either platelet-derived growth factor receptor (PDGFR) or EGFRmt+ expressed by primary tumor cells of human or murine origin (e.g., genetically engineered mouse models of high-grade glioma, neurospheres from human patient brain tumor explants) and/or tumor cell lines of non-neural origin. Dasatinib and gefitinib analogs can be synthesized to enable covalent attachment to several linkers without perturbing the underlying chemical structure defining the active binding site.

Synthetic approaches were validated and the desired linker-drug constructs and NDCs were obtained. HPLC/LCMS methods for NDC characterization and enzyme release assays were also developed. In vitro enzyme drug release assays revealed a number of important structural factors in NDC design. For example, spacing between C dot and linker was varied using different sized PEG chains, and revealed that sufficient spacing between C dot and linker was important to allow for enzyme catalyzed drug release. Similarly, the spacing between linker and drug was also found to be important for enzyme mediated release. Moreover, linker designs utilizing a degradable moiety between the linker and drug exhibited significantly faster release kinetics than those where a simple amide bond was used. In some embodiments, the degradable moiety can be a carbohydrates and/or any linker that can be enzymatically cleaved and/or activated.

Cell-based assays were also performed. Linker-drug constructs and NDCs incorporating either dasatinib or gefitinib analogs were tested against primary brain tumor cells (neurospheres) and/or tumor cell lines metastasizing to the brain (e.g., lung, squamous cell cancers). Phosphorylation levels of EGFRmt+ were reduced or ablated in cell lines exposed to NDCs as well as the free linker-drug constructs, and NDCs exhibited more potent inhibitory activity than the native drug in some cases.

In one aspect, a nanoparticle drug conjugate (NDC) comprising a drug moiety, a linker moiety, and a nanoparticle, wherein the drug moiety is covalently linked to the nanoparticle via the linker moiety is described herein. In certain embodiments, the NDC comprises an amide bond and/or degradable moiety between the linker moiety and the drug moiety. In certain embodiments, the linker moiety comprises a peptide (e.g., a dipeptide). In certain embodiments, the linker moiety provides hydrolysis at the C-terminal end upon protease binding, thereby releasing the drug moiety from the nanoparticle. In certain embodiments, the drug moiety comprises a receptor tyrosine kinase (RTK) inhibitor (e.g., dasatinib or gefitinib, including any analog thereof, e.g., any pharmaceutical and/or therapeutic equivalent thereof, modified to provide attachment to the linker moiety without perturbing underlying chemical structure of an active binding site of the drug moiety). In certain embodiments, the nanoparticle is a newer generation C dot or a C' dot. In another aspect, the invention is directed to a method of detection, prevention, and/or treatment of a disease (e.g., cancer) comprising administration and/or detection of the NDC of any of the embodiments described herein.

Nano-sized drug delivery vehicles are appealing due to (1) their small sizes, enabling trafficking throughout the body as well as within the cells; (2) their high surface area to volume ratios, enabling cargo loading and release; and (3) their tunable surface chemistries, enhancing solubility, controlling binding, and incorporating biologically active functionalities.

In vivo nanoparticle drug delivery is fraught with a host of biophysical and biochemical challenges that can cause particle uptake (opsonization), excretion (kidneys) or non-specific loss (extravasation), and prevent the therapeutic payload from reaching the desired cells. One of the key parameters of a drug delivery construct is its physical size, where smaller particles (e.g., particles less than or equal to about 5 nm hydrodynamic diameter) can extravasate non-specifically, while much larger particles or aggregates (e.g., particles or aggregates greater than or equal to about 500 nm diameter) can become lodged in the microvasculature, rather than being trafficked to their intended targets. For non-biodegradable materials, it is found that there is a preferable diameter range from 5 nm to 10 nm enabling renal filtration as a means of particle removal, while limiting the rate of renal clearance to enable the desired pharmacokinetics. Additionally, it was found that particles of this size regime can also take advantage of an enhanced permeability and retention (EPR) effect, that is, the passive accumulation of macromolecules in tumor microenvironments due to the leaky vasculature.

For example, in certain embodiments, an ultra-small (e.g., having a diameter range from 5 nm to 10 nm), was tested in humans as is described in U.S. Publication No. 2014/0248210 A1, which is hereby incorporated by reference in its entirety. In this example, five patients had no adverse events and the agent was well tolerated over the study period. Pharmacokinetic behavior, expressed as the percentage of the injected dose per gram of tissue (% ID/g), versus time post-injection and the corresponding mean organ absorbed doses, were comparable to those found for other commonly used diagnostic radiotracers. Serial PET imaging of this representative patient showed progressive loss of presumed blood pool activity from major organs and tissues, with no appreciable activity seen by 72-hour post-injection (p.i.). Whole-body clearance half-times in these patients were estimated to range from 13-21 hours. Interestingly, there was no notable localization in the liver, spleen, or bone marrow, in contrast to many hydrophobic molecules, proteins, and larger particle platforms (greater than 10 nm). Although patients were pretreated with potassium iodide (KI) to block thyroid tissue uptake, a higher average absorbed thyroid dose was obtained in this patient relative to other tissues. Particles were also primarily excreted by the kidneys, with both kidney and bladder wall (after thyroid and tumor, see below), demonstrating one of the highest % ID/g values by 72 hrs p.i.; as is often the case for renally excreted radiopharmaceuticals, the bladder wall received a higher average absorbed dose than other major organs and tissues. These findings highlight the fact that renal, rather than hepatobiliary, excretion is the predominant route of clearance from the body.

Epidermal growth factor receptor (EGFR) is used for targeted therapy. EGFR mutations resulting in constitutive activation have been found in 10-35% of metastatic non-small cell lung cancer (NSCLC), and while EGFR inhibitors are effective for systemic disease, control of brain metastases remains limited by drug delivery. EGFR mutations are also found in 40-50% of primary glioblastoma multiforme (GBM)—two prevalent forms of brain cancer. While EGFR-tyrosine kinase inhibitors (TKIs), such as gefitinib, have shown promise in preclinical settings, they have demonstrated to be largely ineffective in brain cancer patients, likely due to poor tissue or central nervous system (CNS) penetration and dose-limiting toxicity.

Gefitinib binds and inhibits the kinase domain active site of EGFR. To utilize gefitinib in the context of NDCs, it is important to incorporate a chemically reactive group that does not significantly perturb drug binding to the kinase domain. X-ray crystallographic and SAR studies revealed that replacing the morpholino-group with an amine does not significantly alter drug activity but provides the needed chemical functionality (amine) for modification and eventual covalent attachment to the C dot or C' dot (FIG. 1A).

EXPERIMENTAL EXAMPLES

One example demonstrates exemplary synthesis of nanoparticle drug conjugates (e.g., silica-based nanoparticle platform with covalently attached drug molecules) and their characterization and preliminary biological evaluations.

Figure 10:
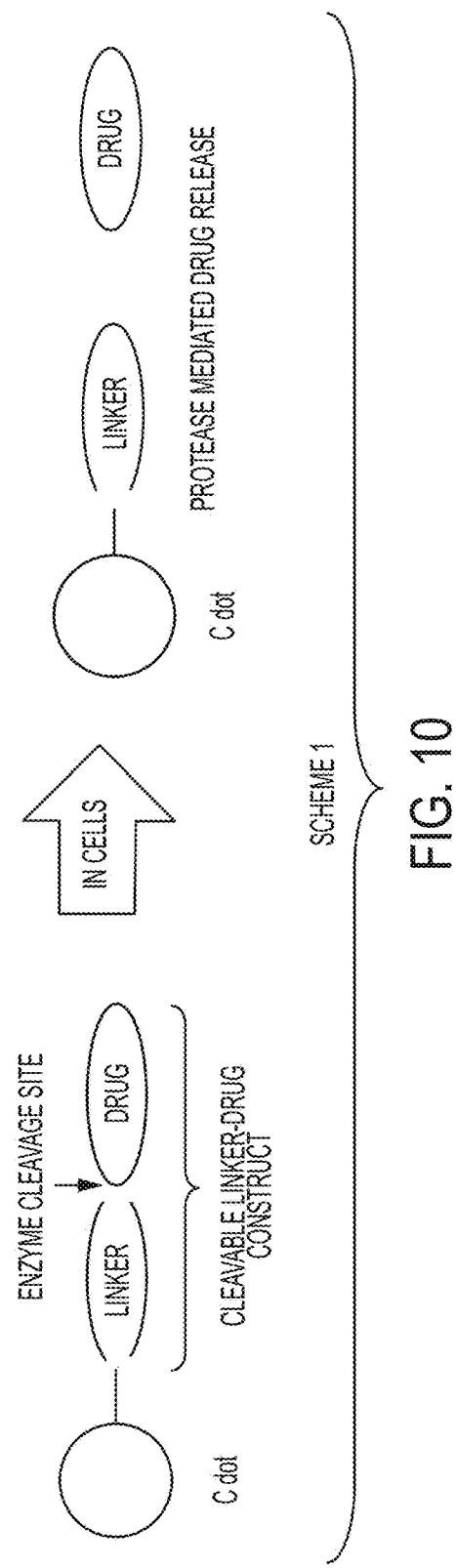
FIG. 10 shows Scheme 1, which illustrates enzyme-mediated drug release from nanoparticle drug conjugate (NDC).
Figure 11:
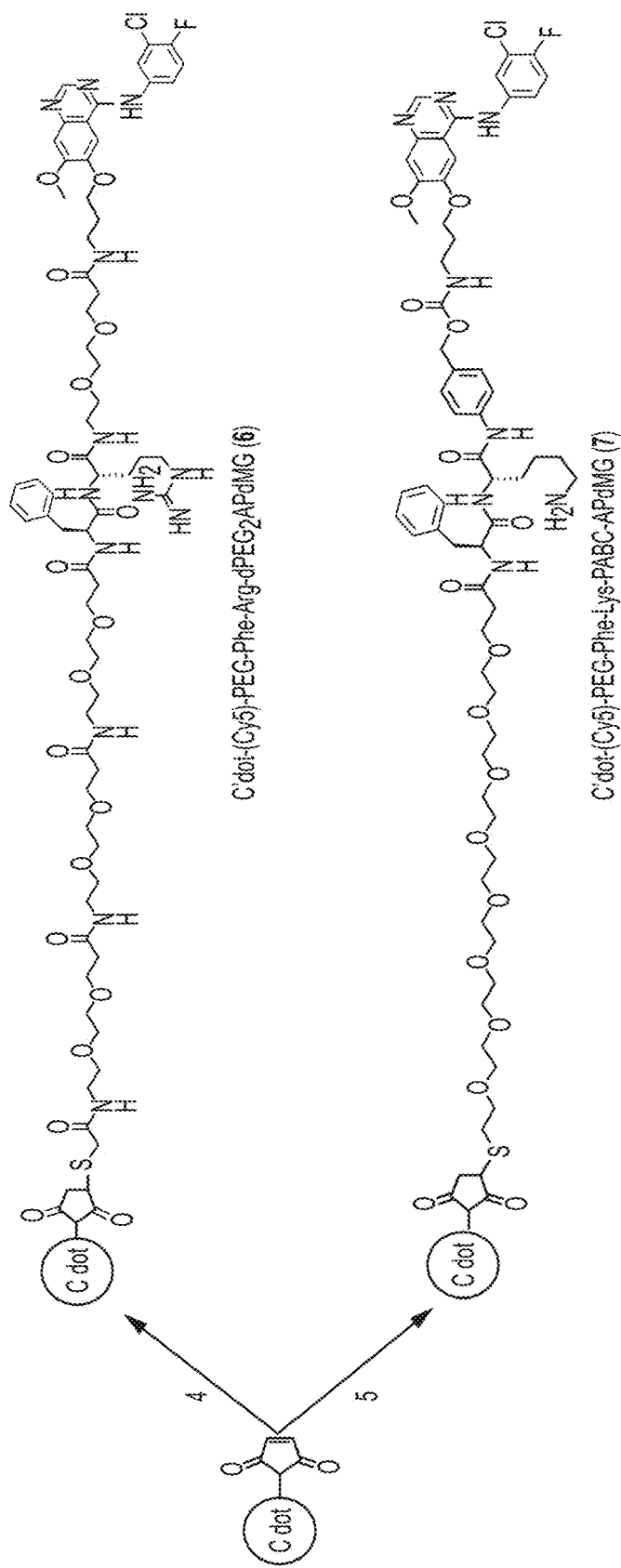
FIG. 11 shows Scheme 2, which illustrates that C'dots-(Cy5)-PEG-mal are reacted with linker-drug constructs Phe-Arg-dPEG2APdMG 4 and Phe-Lys-PABC-APdMG 5 resulting in the NDCs C'dot-(Cy5)-PEG-Phe-Arg-dPEG$_2$APdMG 6 and C'dot-(Cy5)-PEG-Phe-Lys-PABC-APdMG 7.

With the commercial availability of des-morpholino-gefitinib (dMG), the desired aminopropyl-dMG (APdMG) was obtained through a nucleophilic substitution (e.g., in one step) of Boc protected amino propyl bromide, followed by acid deprotection (FIG. 1A, FIG. 10 (Scheme 1)). Additionally, the gefitinib analogue 2, which is described in further detail below, was readily obtained from 1 by coupling Fmoc-dPEG2-COOH, with a subsequent base deprotection step (FIG. 1A, FIG. 11 (Scheme 2)). To ensure that APdMG 1 and dPEG$_2$APdMG 2 have retained activity against EGFR, H1650 cells were treated with the compounds and analyzed by western blot to assess phospho-Tyr168 levels in EGFR. The H1650 cells are a model human tumor-derived non-small-cell lung cancer (NSCLC) line (bronchioalveolar carcinoma), which contain a mutated EGFR (L858R and ΔE746-A750) resulting in constitutive activity of the receptor. Both compounds showed effects similar to gefitinib, with inhibition of phospho-Tyr$^{168}$ at 1 and 10 μM concentrations, while dPEG$_2$APdMG 2 showed reduced activity.

Figure 1B:
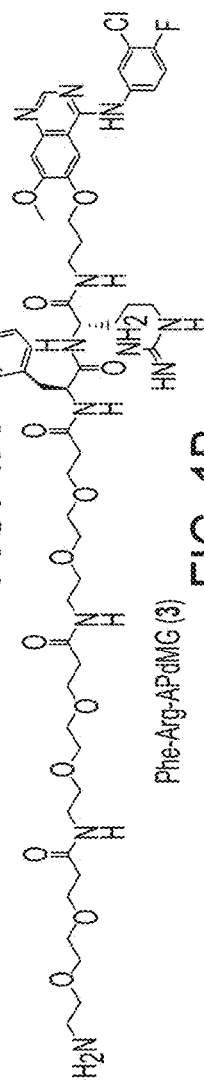
FIG. 1B depicts a chemical structure of linker-drug directly connected through amide bond (Phe-Arg-APdMG 3).
Figure 1C:
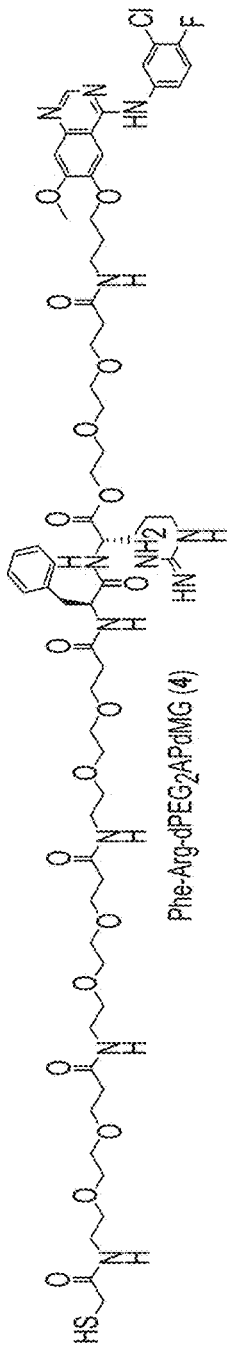
FIG. 1C depicts a chemical structure of linker-drug connected through dPEG$_2$ spacer (Phe-Arg-dPEG$_2$APdMG 4).
Figure 1D:
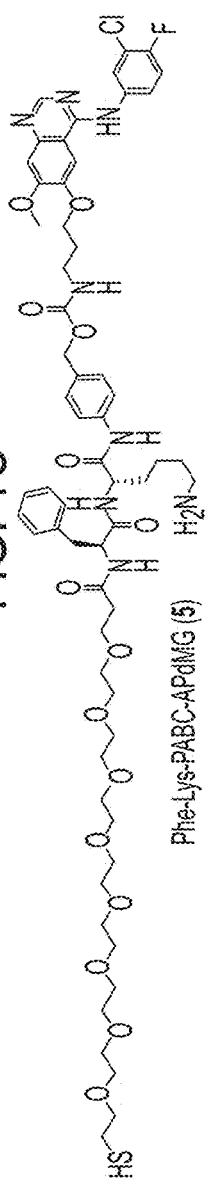
FIG. 1D depicts a chemical structure of linker-drug connected through degradable PABC spacer (Phe-Lys-PABC-APdMG 5)

Three linker types were investigated for C dot based drug delivery (FIG. 1B-1D). The three linker types include dipeptide sequences which utilize proteases for drug release. Proteases recognize and bind the dipeptide leading to hydrolysis at the C-terminal end, releasing the drug component from the linker. Two model proteases were used to evaluate the linker-drug constructs described here, trypsin and cathepsin B. Trypsin was selected as a representative serine protease. It is highly active against peptides containing basic amino acids such as arginine and lysine, and cleaves C-terminal to these residues. Cathepsin B is a cysteine protease with more stringent substrate specificity. The minimal substrate consensus sequence described to date is a dipeptide motif containing hydrophobic and basic residues. Similar to trypsin, cathepsin B cleaves C-terminal to the basic amino acid. The dipeptides phenylalanine-arginine (Phe-Arg) and phenylalanine-lysine (Phe-Lys) are the trypsin/cathepsin B recognition motifs for trypsin and cathepsin, and are included in the linker-drug constructs (FIGS. 1B-D).

The Phe-Arg-APdMG is an example of an approach for obtaining a protease sensitive linker-drug construct (FIGS. 2A and 2B). In such a design, the gefitinib analog 1 is directly attached to the C-terminus of the dipeptide sequence. Compound 3 was synthesized using solid phase peptide synthesis (SPPS) methods, followed by modification of the C-terminus with 2, and a final deprotection step yielding 3 (FIG. 11 (Scheme 3)).

Given the close proximity of the drug component to the dipeptide motif, potential steric problems that could hinder the enzyme from binding and hydrolyzing the linker-drug were addressed. To increase the distance between the dipeptide and drug, APdMG 1 was modified to obtain dPEG$_2$APdMG 2 (FIG. 13, (Scheme 4)). A coupling reaction between the dipeptide component and dPEG$_2$APdMG 2, followed by a deprotection step, afforded Phe-Arg-dPEG$_2$APdMG 4—a linker drug construct containing a short PEG spacer of 10 atoms between the Phe-Arg and the gefitinib analogue.

To retain the increased spacing between the dipeptide and drug components without introducing structural changes to APdMG 1, Phe-Lys-PABC-APdMG 5 was synthesized. This linker incorporates a self-immolative para-aminobenzyloxy carbamate (PABC) group between the peptide and drug (FIGS. 1D and 2A-2C). Upon enzymatic hydrolysis, this group further decomposes into para-aminobenzyl alcohol and CO$_2$, thereby releasing the APdMG. Synthesis of compound 5 begins with Fmoc-Lys(Mtt)-OH (FIG. 13 (Scheme 6)). The protected amino acid is modified with para-aminobenzyl alcohol giving Fmoc-Lys(Mtt)-PABA 18. Upon removal of the Fmoc group and coupling with Fmoc-Phe-OH, the protected dipeptide, Fmoc-Phe-Lys(Mtt)-PABA19 is formed. The free hydroxyl group of the -PABA is then activated with para-nitrophenol carbonate chloride leading to an activated carbonate 20, which is then reacted with APdMG 1 resulting in compound 21. After a round of deprotection and coupling, compound 22 was obtained. The final deprotection step required acidic conditions. However, the para-aminobenzyloxy carbamate group itself is susceptible to decomposition under such conditions (e.g., acidic conditions). Sufficiently mild conditions (e.g., 0.5% TFA) were found to remove the Mtt group from the lysine and the Mmt group from the terminal thiol while preserving the linker to afford the desired product 16. The Mtt group masking the lysine side chain is well suited for this overall synthetic approach as it is stable in the presence of para-nitrophenol carbonate chloride but labile for removal under mild acidic conditions. This is in contrast to the more commonly used hyper-labile Mmt group for lysine side chain protection, which was readily removed in the presence of para-nitrophenol carbonate chloride.

To evaluate the three linker-drug constructs, compounds 3-5 were subjected to enzymatic hydrolysis (Table 1, FIGS. 3A-3C, 4A and 4B). The drug-linker constructs were incubated with either trypsin or cathepsin B and the reaction was monitored by HPLC or LCMS. Trypsin was active against all three constructs: by 60 min complete hydrolysis of Phe-Arg-APdMG 3 resulting in APdMG 1 was observed; only 10 min for complete release of dPEG$_2$APdMG 2 from Phe-Arg-dPEG$_2$APdMG 4, and release of APdMG 1 from Phe-Lys-PABC-APdMG 5. However, when constructs were treated with cathepsin B, no hydrolysis was observed for Phe-Arg-APdMG 3, while Phe-Arg-dPEG$_2$APdMG 4 was completely hydrolyzed leading to the of release dPEG$_2$APdMG 2.

Table 1 below illustrates half lifes obtained by drug release assay for linker-drug constructs.

TABLE 1

| Substrate | Trypsin $t_{1/2}^a$ (min) | Cathepsin B $t_{1/2}^a$ (min) |
|---|---|---|
| Phe-Arg-APdMG (3) | 9 | NH |
| Phe-Arg-dPEG$_2$APdMG (4) | 2 | 110 |
| Phe-Lys-PABC-APdMG (5) | 1 | 1 |

NH—no hydrolysis
$^a$Time when 50% of the drug is released from linker or particle as determined by HPLC at 348 nm.

Figure 4A:
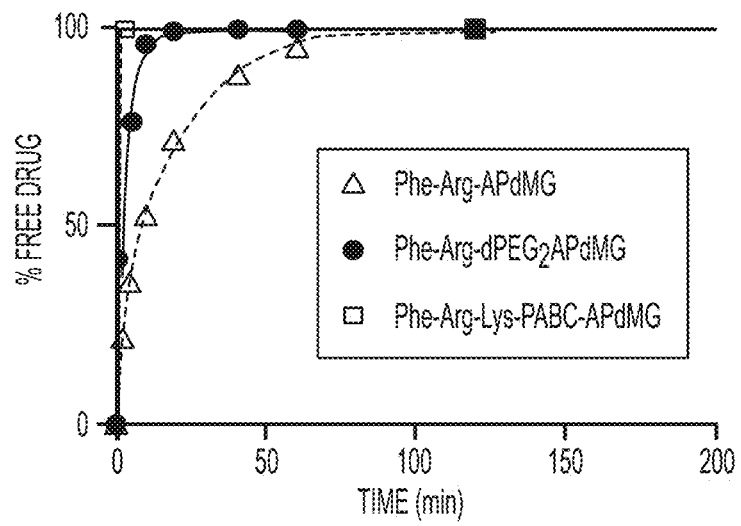
FIGS. 4A and 4B show in vitro drug release assays for free linker-drug constructs Phe-Arg-APdMG, Phe-Arg-dPEG$_2$APdMG, and Phe-Lys-PABC-APdMG, monitored over time by HPLC at 348 nm. % Free Drug is the drug released divided by the initial drug load of the linker-drug construct determined at 348 nm.
Figure 4B:
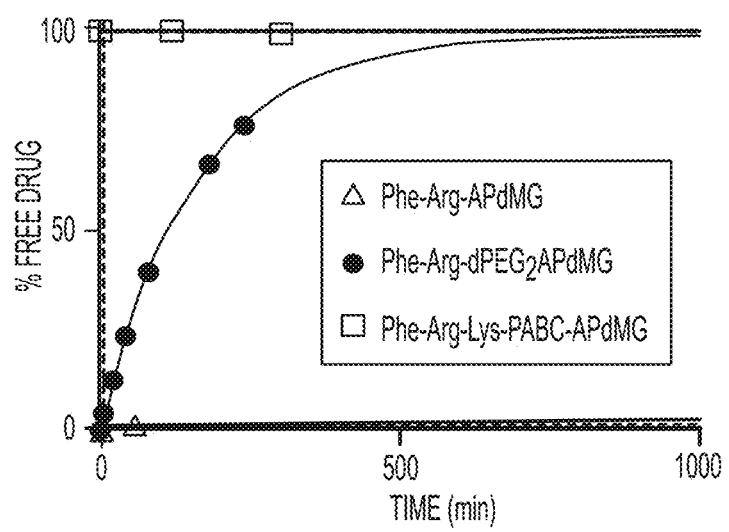

In vitro assays were conducted for compounds 3-5 to obtain drug release profiles and enzyme mediated hydrolysis of the constructs was monitored over different time points (FIGS. 4A and 4B). For the Phe-Arg-APdMG 3, 50% of drug APdMG 1 was released in 9 min, while the Phe-Arg-dPEG$_2$APdMG4 was notably faster with 50% drug release within 2 min. The compound 5 was also fast, requiring less than 1 min for 50% drug release. In the presence of cathepsin B, The Phe-Arg-APdMG 3 proved to be a poor substrate, as no drug release was observed. For the Phe-Arg-dPEG$_2$APdMG 4, 50% of drug was released in 110 min. The Phe-Lys-PABC-APdMG 5 required <1 min for 50% drug, suggesting it to be a highly efficient substrate for the enzyme.

For both trypsin and cathepsin B, the rate of drug release for the three linker-drug constructs follows the same general trend: Phe-Lys-PABC-APdMG 5>Phe-Arg-dPEG$_2$APdMG 4>Phe-Arg-APdMG 3 (fastest to slowest). The results for Phe-Arg-APdMG 3 and Phe-Arg-dPEG$_2$APdMG 4 suggest that the proximity of the drug to the dipeptide unit affects enzyme activity and drug release. Hydrolysis (drug release) is enhanced when the spacing (distance) between the drug and dipeptide is increased through the incorporation of a 10 atom PEG group. This effect is most prominently observed with cathepsin B, which is unable to hydrolyze construct 3. However, by incorporating the 10 atom PEG spacer between the drug and dipeptide 4, hydrolysis and drug release are observed.

To prepare NDCs, maleimide functionalized C' dots (C' dots-(Cy5)-PEG-mal) were synthesized. Silanes modified with the Cy5 fluorophore were prepared and titrated with tetramethylorthosilane (TMOS) into a dilute solution of NH$_4$OH (molar ratio TMOS:Cy5:NH3:H20 is 1:0.001:0.44:1215) and allowed to mix for 24 hours (Urata C, Aoyama Y, Tonegawa A, Yamauchi Y, Kuroda K. Dialysis process for the removal of surfactants to form colloidal mesoporous silica nanoparticles. Chem Commun (Camb). 2009(34): 5094-6) (Yamada H, Urata C, Aoyama Y, Osada S, Yamauchi Y, Kuroda K. Preparation of Colloidal Mesoporous Silica Nanoparticles with Different Diameters and Their Unique Degradation Behavior in Static Aqueous Systems, Chem. Mater. 2012; 24(8):1462-71.) (Wang J, Sugawara-Narutaki A, Fukao M, Yokoi T, Shimojima A, Okubo T. Two-phase synthesis of monodisperse silica nanospheres with amines or ammonia catalyst and their controlled self-assembly. ACS Appl Mater Interfaces. 2011; 3(5):1538-44.) This resulted in a Cy5 encapsulated silica particle, the surface of which was further PEGylated and functionalized with maleimide groups by treatment with PEG-silane (500 g/mole) (Suzuki K, Ikari K, Imai H. Synthesis of silica nanoparticles having a well-ordered mesostructured using a double surfactant system. J Am Chem Soc. 2004; 126(2): 462-3.) and maleimide-PEG-silane (molar ratio PEG-silane: TMOS:mal-PEG-silane of 1:2.3:0.006). After 48 hours, the reaction mixture was dialyzed, filtered and purified by gel filtration. Nanoparticles were characterized by fluorescence correlation spectroscopy (FCS), transmission electron microscopy (TEM), and analytical HPLC for diameter, morphology, and overall purity, respectively. The resulting C' dots were less than 10 nm in diameter with narrow particle size distributions (FIGS. 16A-16D).

NDCs incorporating the linker-drugs 4 and 5 (e.g., C' dot-(Cy5)-PEG-Phe-Arg-dPEG$_2$APdMG (6) and C' dot-(Cy5)-PEG-Phe-Lys-PABC-APdMG (7)) were obtained by adding Phe-Arg-dPEG$_2$APdMG (4) and Phe-Lys-PABC-APdMG (5) to the C' dots-(Cy5)-PEG-mal to allow the terminal thiols on the constructs to react with maleimide groups on the particles (Scheme 2). The NDC products were isolated following purification by gel filtration and yielding NDCs 6 and 7 and characterized by TEM and HLPC (FIG. 16A and FIG. 16B). Analytical HPLC was used to assess the presence of contaminants as well as determine the number of drug molecules per particle or drug to particle ratio (DPR) (Table 2). The concentration of gefitinib analogs can be readily measured at 348 nm, while particle concentrations can be obtained at 650 nm, due to the Cy5 embedded within the C' dots. While the average DPR proved to be modest, the NDCs exhibited measurable heterogeneity where DPR estimates ranged from less than 1 to greater than 15. Precipitation of NDCs were not observed, as might be expected due to the poor solubility of the gefitinib analogues. FCS was used to assess changes in the particle size due to linker-drug conjugation. As shown in Table 2, NDCs showed a minimal increase in diameter over the base mal-C' dot.

Table 2 below illustrates a summary of nanoparticle characterization.

TABLE 2

| Particle | Diameter[a] (nm) | DPR Average[b] (Range) |
|---|---|---|
| C'dot-(Cy5)-PEG-Mal | 6.3 | — |
| C'dot-(Cy5)-PEG-Phe-Arg-dPEG$_2$APdMG (6) | 6.4 | 5 (1-15) |
| C'dot-(Cy5)-PEG-Phe-Lys-PABC-APdMG (7) | 6.5 | 2 (1-15) |

DPR—drug to particle ratio
[a]Determined by FCS
[b]Determined by HPLC

Figure 5A:
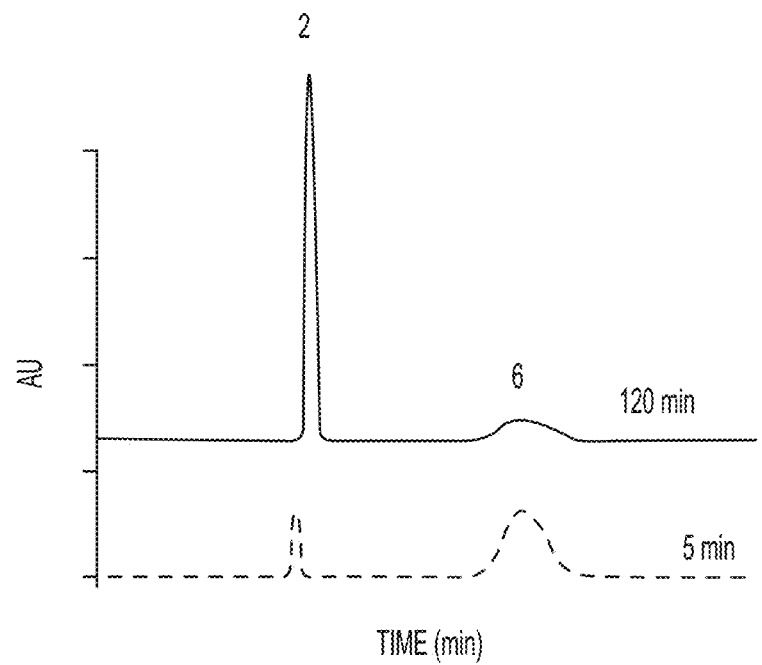
FIGS. 5A and 5B show representative HPLC profiles of in vitro drug release from NDCs in the presence of trypsin. NDCs were treated with trypsin then analyzed by HPLC after 5 and 120 min. Data indicates that compounds 2 or 3 are released from the C'dots. Trypsin assays were conducted in 10 mM phosphate buffer (pH 7.2) at 37° C. HPLC analysis at 348 nm.
Figure 5B:
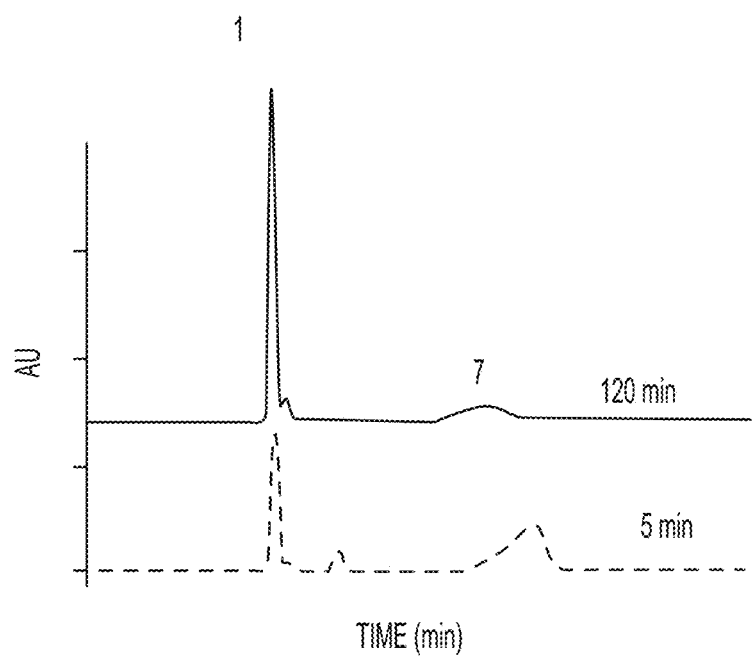
Figure 6A:
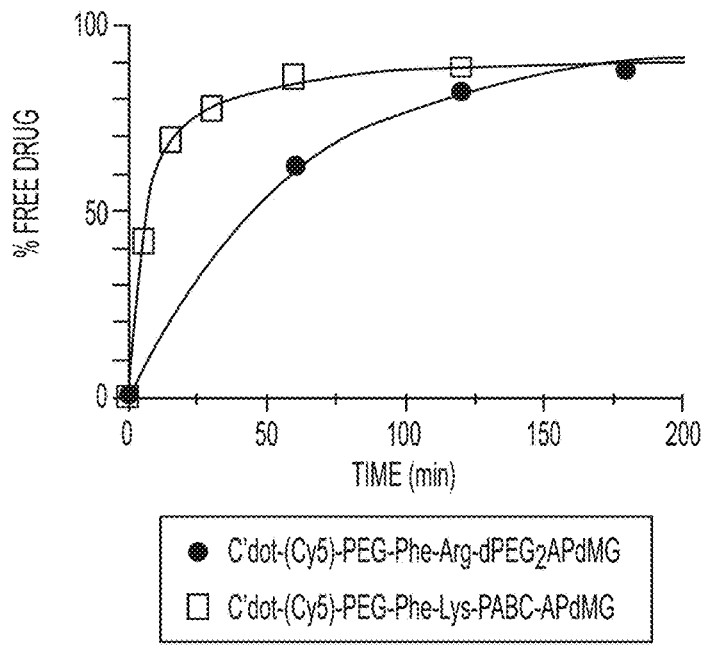
FIGS. 6A and 6B depict in vitro drug release from NDCs in the presence of enzymes. Enzymatic reactions were monitored over time by HPLC at 348 nm. Trypsin assays were conducted in 10 mM phosphate buffer (pH 7.2) at 37° C.; cathepsin B assays were conducted in 25 mM sodium acetate buffer (pH 5.0) at 37° C.
Figure 6B:
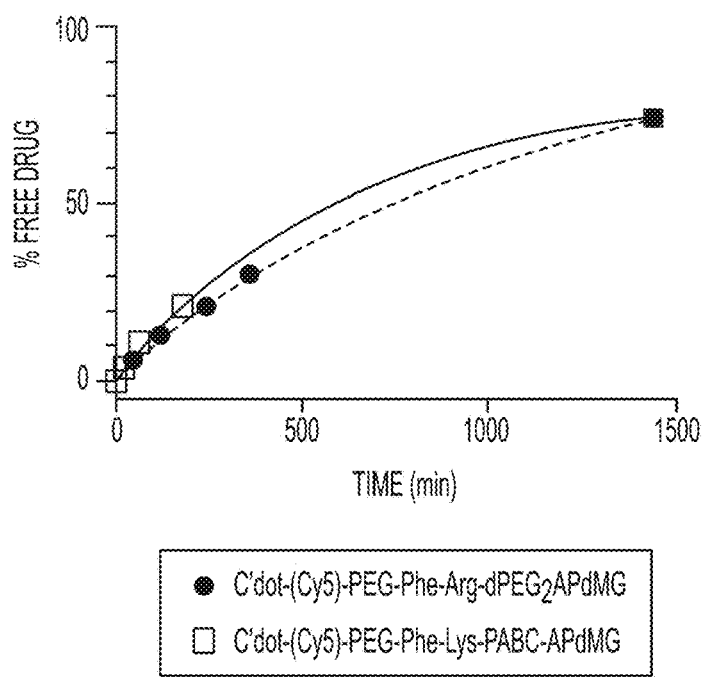

Enzyme dependent drug release over time was measured for C' dot-(Cy5)-PEG-Phe-Arg-dPEG$_2$APdMG and C' dot-(Cy5)-PEG-Phe-Lys-PABC-APdMG to obtain in vitro drug release profiles (FIGS. 6A and 6B). Representative HPLC data demonstrating drug release with trypsin is shown in FIGS. 5A and 5B. NDCs 6 and 7 were excellent substrates for trypsin, requiring 44 min and 6 min, respectively, to achieve 50% drug release (FIG. 6A, Table 1). In the presence of cathepsin B, release kinetics were markedly slower for both NDCs: 50% of drug release was achieved in 560 mM for NDC 6 and 510 min for NDC 7 (FIG. 6B, Table 1). Taken together, the data demonstrates the accessibility of the linker-drug constructs on the particle surface, leading to the controlled release of the drug components.

The stabilities of NDCs were evaluated in aqueous conditions under acidic and neutral pH (5.0 and 7.2) at 37° C. Both NDC 6 and 7 exhibited no degradation or drug release for 48 hours, as measured by HPLC. Thiol-maleimide based conjugations have drawn scrutiny due to the observed loss of linker drug constructs from antibody drug conjugates due to possible reverse Michael or thiol exchange reactions that can occur in vivo. To assess in vitro stability of the NDCs in the presence of excess thiols, NDC7 was incubated with 30 mM gluthathione at 37° C. for 48 hours at pH 7.2. Less than 5% of the linker-drug was separated from the C dot after 48 hours (Table 4).

Table 3 below illustrates half lifes obtained by drug release assay for linker-drug constructs.

TABLE 3

| Substrate | Trypsin $t_{1/2}$[a] (min) | Cathepsin B $t_{1/2}$[a] (min) |
|---|---|---|
| C'dot-(Cy5)-PEG-Phe-Arg-dPEG$_2$APdMG (6) | 44 | 560 |
| C'dot-(Cy5)-PEG-Phe-Lys-PABC-APdMG (7) | 6 | 510 |

[a]Time when 50% of the drug is released from linker or particle. Determined by HPLC Table 4 below illustrates NDC stability data.

TABLE 4

| Particle | pH 5.2[a] 48 hr | pH 7.2[b] 48 hr | Glutathione[c] 48 hr | Media 18 hr |
|---|---|---|---|---|
| NDC 6 | ~1% | ~2% | ~5% | <5% |
| NDC 7 | ~6% | ~2% | ~4% | <1% |

Figure 7:
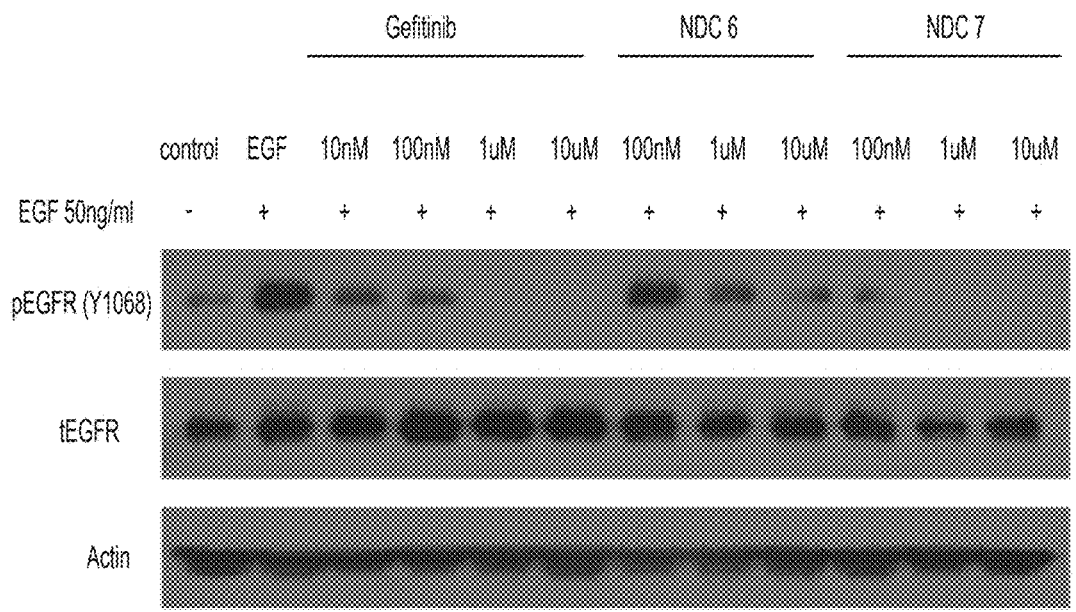
FIG. 7 shows western blot analysis of H1650 cells treated with gefitinib, C'dot-(Cy5)-PEG-Phe-Arg-dPEG$_2$APdMG 6, and C'dot-(Cy5)-PEG-Phe-Lys-PABC-APdMG 7. Cells treated with gefitinib or specified NDC at indicated concentrations for 18 hrs followed by EGF (50 ng/mL) for 5 minutes (pEGFR—phosphorylated EGFR; tEGFR—total EGFR).
Figure 8:
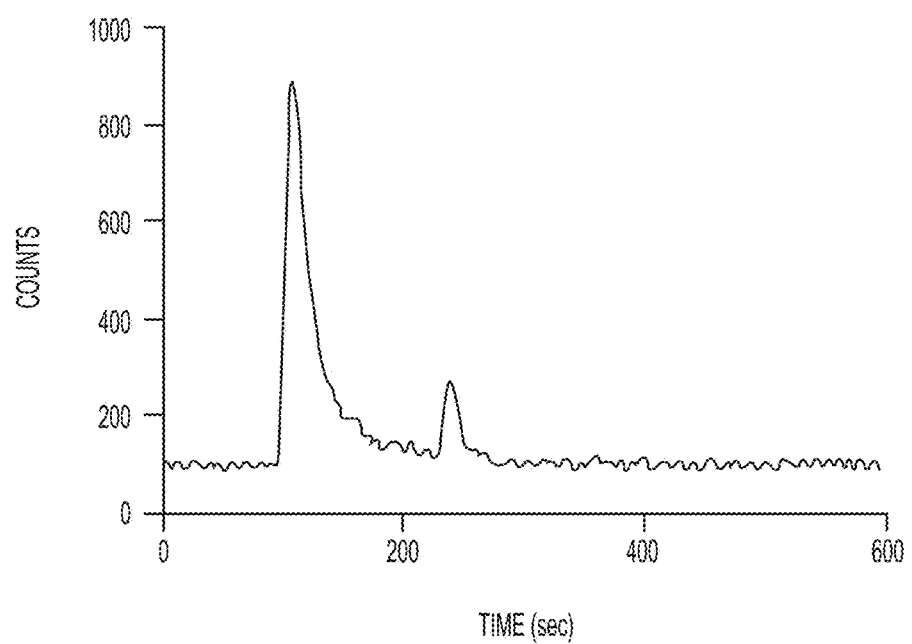
FIG. 8 shows radioGPC of C'dot-(Cy5)-PEG-Phe-Arg-dPEG$_2$-Gly-D-Tyr($^{131}$I)-APdMG 8. Radiochemical yield of >90% based on peak integrations. The smaller peak is presumed to be residual free $^{131}$I.

[a]25 mM sodium acetate buffer
[b]50 mM phosphate buffer
[c]10 mM glutathione (reduced) in 50 mM phosphate buffer
[d]DEM, serum free, 18 hrs after cell treatment The biological activities of C' dot-(Cy5)-PEG-Phe-Arg-dPEG$_2$APdMG and C' dot-(Cy5)-PEG-Phe-Lys-PABC-APdMG were assessed by treatment of H1650 cells followed by western blot detection of phospho-Tyr$^{168}$ in EGFR and compared with gefitinib. Serum starved cells were incubated with each compound over a period of 18 hours, then subject to EGF stimulation. The gefitinib control exhibited a dose dependent decrease in Tyr$^{168}$ phosphorylation of EGFR with complete ablation at 1 µM (FIG. 7). NDCs 6 and 7 also showed dose dependent inhibition; cells treated with NDC 6 showed detectable levels of phospho-Tyr$^{168}$ at 10 µM. In contrast NDC7 exhibited good activity, with significant reduction of phospho-Tyr$^{168}$ at 100 nM, and complete ablation at NDC concentrations of 1 µM. Given the possibility that premature drug release can occur and lead to the observed decreases in phospho-Tyr$^{168}$EGFR, the stability of the NDCs used in these assays were monitored. An aliquot of the media with NDC 6 or 7 (10 µM) used for treating the H1650 cells for 18 hours was analyzed by HPLC. Both particles proved to be stable under these conditions as no free drug was detected in the media and NDCs were intact (Table 3). In addition to the NDCs 6 and 7, incorporation of a secondary imaging modality for eventual in vivo studies was investigated. A linker-drug construct with Phe-Arg-dPEG$_2$-D-Tyr-aminopropyl-dMG was synthesized incorporating a D-tyrosine residue with the drug component for attaching a radiolabel (compounds 23 and 24). The NDC C' dot-(Cy5)-PEG-Phe-Arg-dPEG$_2$-D-Tyr-APdMG was prepared, and successfully radioiodinated with $^{131}$I at >90% radiochemical purity (FIG. 8).

Reagents:

Solvents and reagents purchased from commercial sources were used without further purification. Acetonitrile, diethyl ether, dimethylformamide (DMF), ethyl acetate, hexanes, hexafluoroisopropanol (HFIP), methanol, methylene chloride (DCM), and trifluoroacetic acid (TFA) were obtained from Fisher. Dimethylsulfoxide (DMSO), diisopropylethylamine (DIEA), triethylamine (TEA), potassium carbonate, N-(tert-butyloxycarbonyl)-aminopropylbromide, (3-aminopropyl)triethoxysilane (APTES), (3-mercaptopropyl)trimethoxysilane (MPTMS), tetramethyl orthosilicate (TMOS), bovine trypsin, and were purchased from Sigma-Aldrich. 0-Des-morpholinopropyl gefitinib was obtained from Toronto Research Chemicals (TRC). 2-(7-Aza-1H-benzotriazole-1-yl)-1,1,3,3-tetramethyluronium hexafluorophosphate (HATU) was purchased from Genescript. Chlorotrityl-resins and protected amino acids (Fmoc-Arg-OH, Fmoc-Lys(Mtt)-OH, Fmoc-Phe-OH) were obtained from EMD Chemicals. Fmoc-N-dPEG$_2$OH, Mmt-S-dPEG$_8$-OH, mal-dPEG$_{12}$-NHS were purchased from Quanta Biosciences. Cy5 maleimide and Superdex 200 (prep grade) was obtained from GE Life Sciences. DMSO-d and CDCl$_3$ were purchased from Cambridge Isotopes. Solid-phase synthesis was conducted in polypropylene fritted syringes from Torviq. Silica, TLC plates, 4 g, 12 g, 24 g, and 40 g RediSep Rf normal phase cartridges were obtained from Teledyne ISCO.

Flash Chromatography:

Normal phase (silica gel) purifications were conducted on a Teledyne ISCO CombiFlash Rf using 4 g, 12 g, 24 g, and 40 g cartridges.

Analytical HPLC:

Samples were run on a Waters Alliance HPLC System or Autopure LCMS System (2767 Sample Manager, 2996 Photodiode Array Detector, 2420 ELS Detector, Micromass ZQ, 2525 Binary Gradient Module, Column Fluidics Organizer, 515 HPLC Pump, Pump Control Module II) using a linear gradient of 5-95% acetonitrile in water (0.5% TFA) for 10 minutes at 1.2 mL/min, on either a C4 or C18 4.6×50 mm reversed phase XBridge analytical column (Waters). Samples were analyzed at either 348 nm or 650 nm.

Preparative HPLC:

Samples were purified on either a Waters Preparative System (2996 Photodiode Array Detector, 2545 Binary Gradient Module) or Autopure LCMS System using a linear gradient of 5-95% acetonitrile in water (0.5% TFA) for 30 minutes at 20 mL/min on a C18 19×150 mm reversed phase XBridge preparative column (Waters). Samples were analyzed at either 220 or 348 nm.

Nuclear Magnetic Resonance (NMR);

$^1$H-NMR and $^{13}$C-NMR data were obtained on a Bruker Ultrashield 500 Plus.

Drug Release Assays with Trypsin:

Assays were conducted in 25 mM phosphate buffer (pH 7.2) at 37° C., with 25 µM NDC (e.g., 6 or 7) or free linker-drug (e.g., 3, 4, or 5) and 200 nM trypsin. For analysis, 70 µL portions were removed and quenched with acid (HCl) at specified time points (e.g., 5, 15, 30, 60, 120 minutes or longer) then run on HPLC/LCMS. NDCs were stored in water at 4° C. Trypsin stocks were prepared as follows: 1 mg of trypsin was dissolved in 1 mL water, aliquoted, then immediately flash frozen and stored at −80° C. for up to four weeks. Enzyme activity was tested prior to drug release assay using the substrate Z-Arg-Arg-para-nitro-aniline. The % Free Drug (FIGS. 3 and S3) is the quantity of free drug divided by the initial quantity of drug loaded for the linker-drug construct or NDC. The quantity of free drug is determined by area of the HPLC peak corresponding to the released drug at 348 nm. The quantity of drug loaded is the area of the HPLC peak, at 348 nm, for the linker-drug construct or NDC prior to enzyme treatment. As the C'dot-(Cy5)-PEG-mal has background absorbance at 348 nm, a background subtraction for the NDC is necessary. All buffers and solutions were prepared using ultra-pure water (18 MΩ-cm resistivity).

Drug Release Assays with Cathepsin B:

Assays were conducted in 25 mM sodium acetate buffer (pH 5.0) at 37° C., with 25 µM NDC (e.g., 6 or 7) or free linker-drug (e.g., 3, 4, or 5) and 200 nM cathepsin B. No DTT was used for this assay. For analysis, 70 µL portions were removed and quenched with acid (HCl) at specified time points (e.g., 5, 15, 30, 60, 120 minutes or longer) then run on HPLC/LCMS. NDCs were stored in water at 4° C. Cathepsin B stocks were prepared as follows: 1 mg of cathepsin B was dissolved in 1 mL 50 mM sodium acetate and 2.5 mM EDTA, aliquoted, then immediately flash frozen and stored at −80° C. for several weeks. Enzyme activity was tested prior to drug release assay using the substrate Z-Arg-Arg-para-nitro-aniline. The % Free Drug (FIGS. 4A, 4B, 6A and 6B) is the quantity of free drug divided by the initial quantity of drug loaded for the linker-drug construct or NDC, as described in the previous paragraph. All buffers and solutions were prepared using ultra-pure water (18 MΩ-cm resistivity).

NDC Stability Assays:

Assays were conducted in either 25 mM sodium acetate buffer (pH 5.0) or 50 mM phosphate buffer (pH 7.2) with 7.5 µM NDC (e.g., 6 or 7) and incubated at 37° C. for up to 48 hours. 10 mM Glutathione (reduced) in phosphate buffer (pH 7.2) was also evaluated. 20 µL aliquots were then analyzed by HPLC. For one experiment, after H1650 cells were treated with 10 µM NDC (see the phosphoEGFR assay below) in serum free DEM for 18 hours, the media was recovered and analyzed by HPLC.

PhosphoEGFR Assay with H1650 Cells:

H1650 cells were seeded (1.5 million cells) in 6-well plates with 2 ml of 10% FBS DEM medium and grown for 24 hrs. Cells were washed with 1 mL of serum free DEM medium, then incubated with gefitinib or NDCs at indicated concentrations overnight (18 hrs). Cells were then treated with 50 ng/mL EGF for 5 minutes, then washed with 1 mL of PBS. Trypsin (0.5 ml, 0.25%) was added to each well, and incubated until cells detached (~5 min). 1 mL of 10% FBS DEM medium was added to wells, and cells were transferred to 15 mL conical tubes containing 10 mL of 10% FBS DEM medium. Cells were spun down at 3000 rpm for 5 minutes at 4° C. The cell pellets were washed with 1 mL cold PBS, transferred to 1.5 mL tubes, and spun down. PBS was decanted and 70 µL of RIPA (containing protease and phosphatase inhibitors) was added to the pellet, titurated, and incubated for 10 minutes on ice. Tubes were spun at maximum speed for 10 minutes at 4° C. Lysate was transferred to new 1.5 ml tubes and stored at −80° C. Protein concentrations were determined by the Bradford assay. Western blots were run on a Life Technologies apparatus, using Novex 8% tris-glycine gels (1.5 mm×15 wells), tris-glycine SDS running buffer, NuPAGE transfer buffer, 0.1% Tween-20 in 1×TBS washing buffer, and 5% milk in the washing buffer as the blocking buffer. Primary antibodies were applied as follows: anti-phosphorylated-EGFR (pEGFR, Tyr$^{1068}$) (1:1000 dilution; Cell Signaling), anti-EGFR (D38B1) (1:5000 dilution; Cell Signaling), monoclonal anti-β-actin clone AC-15 (1:5000 dilution; Sigma-Aldrich). Secondary antibodies applied were goat anti-mouse IgG-HRP (1:10000 dilution; Santa Cruz Biotechnology) and goat anti-rabbit IgG-HRP (1:5000 dilution; Santa Cruz Biotechnology).

Figure 12:
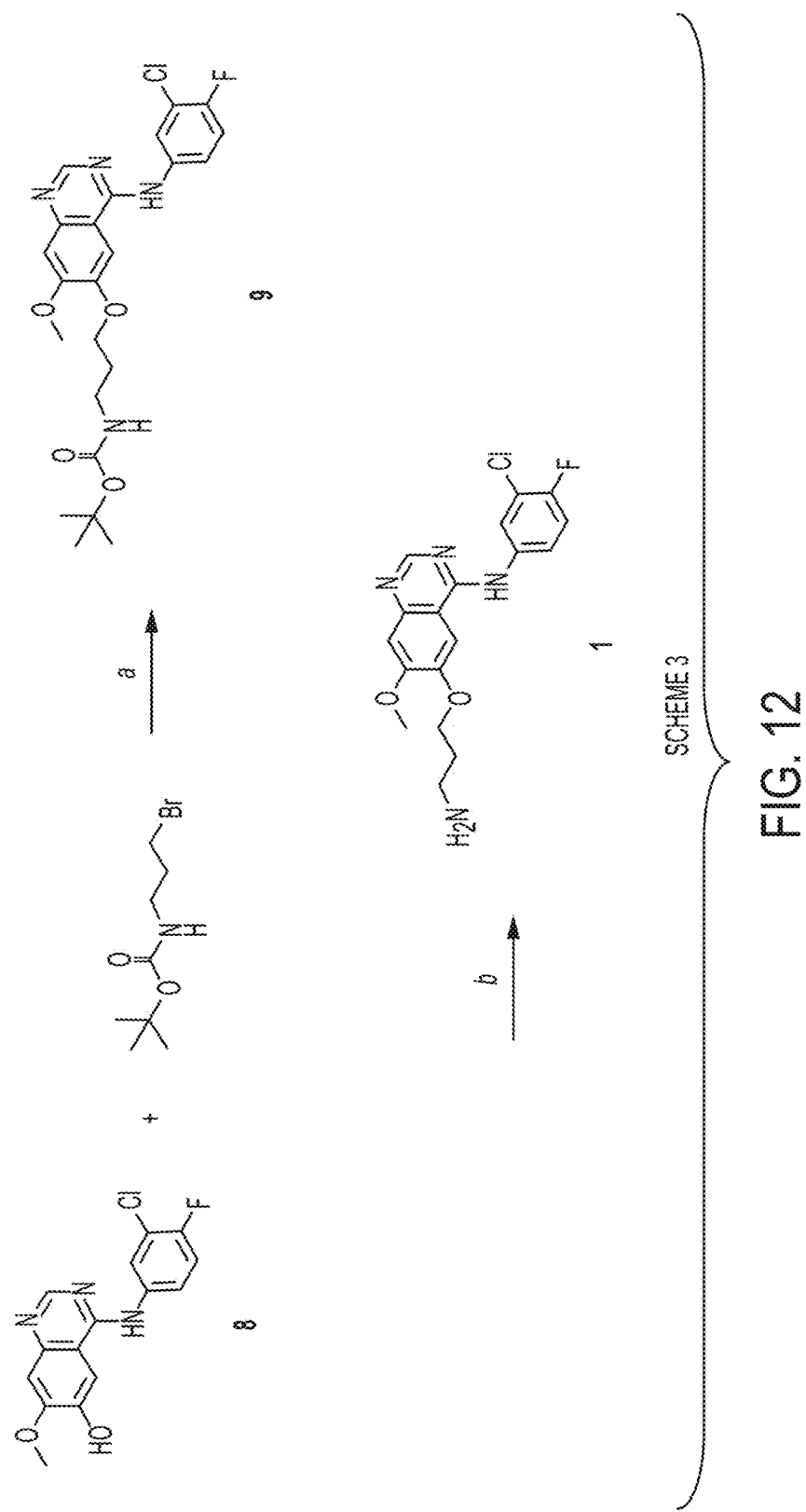
FIG. 12 shows Scheme 3, which illustrates a synthesis process of APdMG 1.

Preparation of O-Des-Morpholino-Gefitinib, dMG (8, in FIG. 12 (Scheme 3))

Compound was obtained commercially.

$^1$H-NMR (500 MHz, DMSO-d6): δ 9.69 (s, 1H), 9.47 (s, 1H), 8.48 (s, 1H), 8.22 (dd, J=6.9, 2.7 Hz, 1H), 7.84 (ddd, J=9.1, 4.4, 2.7 Hz, 1H), 7.78 (s, 1H), 7.41 (t, J=9.1 Hz, 1H), 7.22 (s, 1H), 3.98 (s, 3H). $^{13}$C-NMR (500 MHz, DMSO-d6): δ 155.83, 153.91, 151.89, 146.73, 146.20, 122.74, 121.69, 116.50, 116.33, 109.51, 107.18, 105.25, 55.92. ESI-MS (m/z) for $C_{15}H_{11}ClFN_3O_2$ (exact mass 319.1): [M+H]$^+$ calc. 320.1, obs. 320.2.

Synthesizing N-(tert-Butyloxycarbonyl)-aminopropyl-dMG (9, in FIG. 12 (Scheme 3))

500 mg of compound 8 was dissolved in 100 mL of anhydrous DMF. K$_2$CO$_3$ (mg, mmol) was added to the solution. The reaction proceeded at 60° C. for 16 hrs and checked by TLC and/or HPLC. The solvent was removed in vacuo leaving a brown oil, which was flash purified on a 24 g RediSep Rf normal phase cartridge using a linear gradient of DCM to 20% MeOH in DCM. The final product was isolated as a white solid (312 mg, 62% yield).

$^1$H-NMR (500 MHz, DMSO-d6): δ 9.57 (s, 1H), 8.49 (s, 1H), 8.12 (dd, J=6.8, 2.7 Hz, 1H), 7.81 (m, 1H), 7.44 (t, J=9.1 Hz, 1H), 7.20 (s, 1H), 6.92 (t, J=5.7 Hz, 1H), 4.17 (t, J=6.0 Hz, 2H), 3.95 (s, 3H), 3.15 (q, J=6.5 Hz, 2H), 1.95 (p, J=6.5 Hz, 2H), 1.38 (s, 9H). $^{13}$C-NMR (500 MHz, DMSO-d6): δ 156.01, 155.59, 154.39, 152.61, 146.92, 123.40, 122.29, 118.62, 116.54, 116.37, 107.23, 102.59, 77.51, 66.69, 55.84, 37.22, 35.75, 28.95, 28.22. ESI-MS (m/z) for $C_{23}H_{26}ClFN_4O_4$ (exact mass 476.2): [M+H]$^+$ calc. 477.2, obs. 477.3.

Preparation of Aminopropyl-O-des-morpholino-gefitinib, APdMG (1, in FIG. 1A and FIG. 12 (Scheme 3))

Compound 9 (100 mg, 0.21 mmol) was treated with 1 mL TFA:water (9:1) for 30 min. The TFA:water was removed in vacuo, leaving a light yellow oil. The oil was washed with diethyl ether, then dissolved in a solution of water:acetonitrile (1:1), frozen and lyophilized. A tan solid was obtained (TFA salt, 98 mg, 95% yield).

$^1$H-NMR (500 MHz, DMSO-d6): δ 10.73 (s, 1H), 8.80 (s, 1H), 8.03 (s, 1H), 8.05-8.00 (m, 1H), 7.88 (s, 3H), 7.72 (ddd, J=9.0, 4.3, 2.6 Hz, 1H), 7.54 (t, J=9.0 Hz, 1H), 7.35 (s, 1H), 4.27 (t, J=5.9 Hz, 2H), 4.00 (s, 3H), 3.04 (p, J=6.7, 6.3 Hz, 2H), 2.13 (dt, J=12.2, 6.0 Hz, 2H). $^{13}$C-NMR (500 MHz, DMSO-d6): δ 158.02, 148.80, 116.96, 116.79, 107.60, 103.66, 66.17, 56.42, 36.39, 26.59. ESI-MS (m/z) for $C_{18}H_{18}ClFN_4O_2$ (exact mass 376.1): [M+H]$^+$ calc. 377.1, obs. 377.2.

Figure 13:
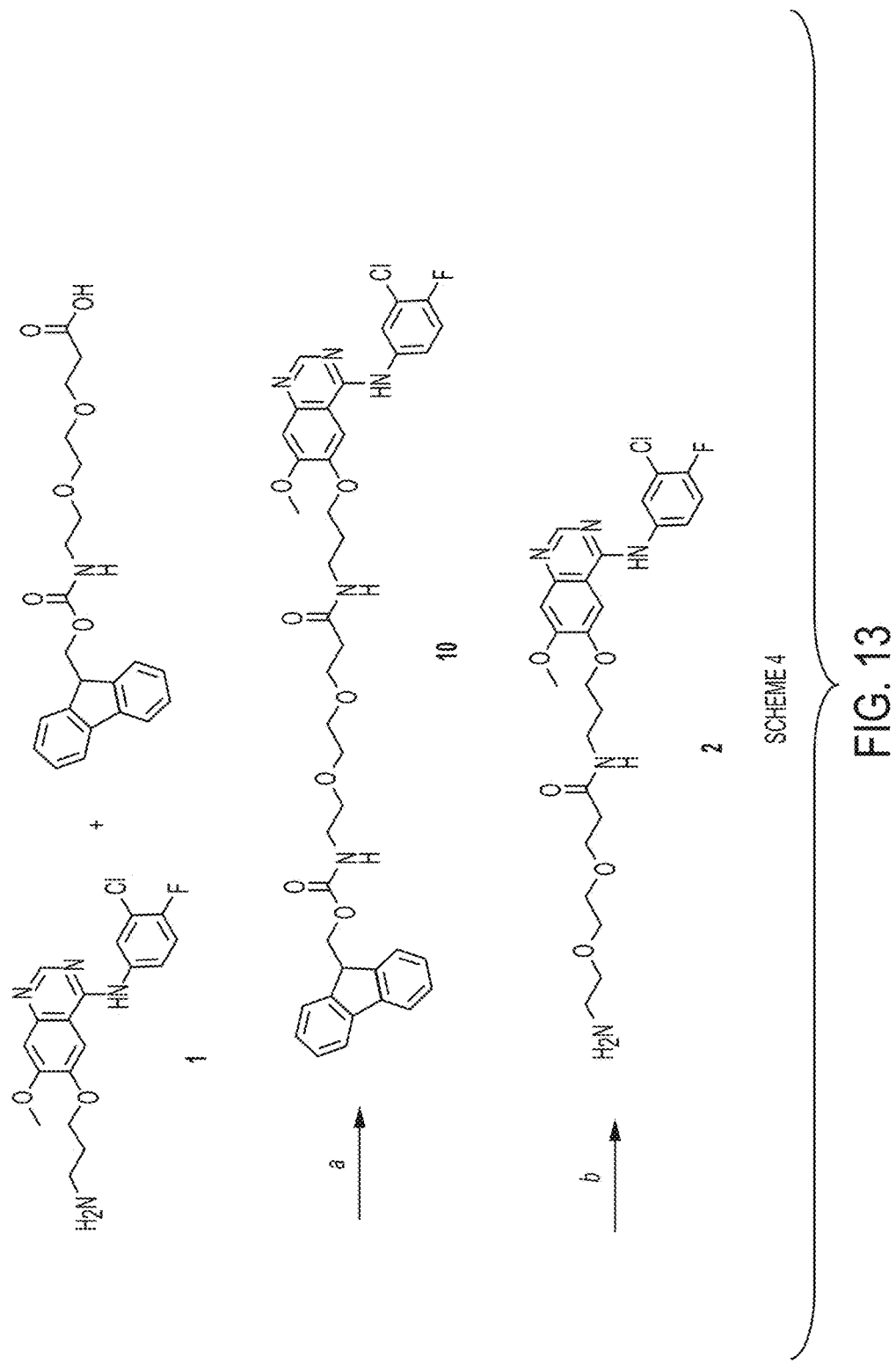
FIG. 13 shows Scheme 4, which illustrates a synthesis process of dPEG$_2$APdMG 2.

Preparation of 9-Fluorenylmethoxycarbonyl-N-amido-dPEG$_2$-aminopropyl-dMG, Fmoc-dPEG$_2$APdMG (10, in FIG. 13 (Scheme 4))

A solution containing dPEG$_2$APdMG 2 (25 mg, 0.05 mmol, TFA salt) and Fmoc-N-amido-dPEG$_2$-COOH (20 mg, 0.05 mmol) in DMF (500 μL) was prepared. DIEA (19 mg, 0.15 mmol, 26 μL) was added followed by a solution of HATU (19 mg, 0.05 mmol) in DMF (100 μL). The reaction proceeded for 30 min at room temp, and determined complete by LCMS. The volume was reduced in vacuo, and purified by silica gel chromatography using a gradient of ethyl acetate and 10% methanol in ethyl acetate. Fractions were collected, pooled and solvent removed in vacuo. The isolated product was a white solid (84% yield).

$^1$H-NMR (500 MHz, DMSO-d6): δ 9.55 (d, J=10.7 Hz, 1H), 8.51 (d, J=2.4 Hz, 1H), 8.18-8.07 (m, 1H), 7.96 (t, J=5.5 Hz, 1H), 7.87 (d, J=7.6 Hz, 2H), 7.83-7.76 (m, 2H), 7.67 (d, J=7.5 Hz, 2H), 7.49-7.36 (m, 3H), 7.31 (td, J=7.5, 1.2 Hz, 3H), 7.21 (s, 1H), 4.28 (d, J=6.9 Hz, 2H), 4.24-4.10 (m, 3H), 3.94 (s, 3H), 3.60 (t, J=6.4 Hz, 2H), 3.46 (s, 4H), 3.36 (t, J=6.0 Hz, 2H), 3.27 (q, J=6.6 Hz, 2H), 3.10 (q, J=5.9 Hz, 2H), 2.32 (t, J=6.5 Hz, 2H), 1.97 (p, J=6.5 Hz, 2H). $^{13}$C-NMR (500 MHz, CDCl$_3$): δ 170.08, 143.85, 127.54, 126.98, 125.10, 120.05, 102.60, 69.42, 69.04, 66.78, 66.58, 55.87, 46.69, 40.01, 39.94, 39.85, 39.77, 39.68, 39.60, 39.51, 39.43, 39.35, 39.25, 39.18, 39.07, 39.01, 36.16, 35.69, 28.67, 0.08. ESI-MS (m/z) for $C_{40}H_{41}ClFN_5O_7$ (exact mass 757.27): [M+H]$^+$ calc. 758.3, obs. 758.4.

Preparation of Amino-dPEG$_2$-aminopropyl-dMG, dPEG$_2$APdMG (2, in FIG. 1A and FIG. 13 (Scheme 4))

Compound 10 (10 mg, 0.013 mmol) was dissolved in 30% piperidine in DMF (1 mL) and allowed to react for 15 min at room temperature. The solvent was removed in vacuo, dissolved in water/acetonitrile and purified by reversed phase (C18) HPLC. The product was recovered as a white powder (7 mg, 80% yield).

$^1$H-NMR (500 MHz, DMSO-d6): δ 10.66 (s, 1H), 8.78 (s, 1H), 8.05-7.97 (m, 3H), 7.80 (s, 3H), 7.72 (ddd, J=9.0, 4.3, 2.6 Hz, 1H), 7.54 (t, J=9.1 Hz, 1H), 7.32 (s, 1H), 4.20 (t, J=6.1 Hz, 2H), 4.00 (s, 3H), 3.65-3.48 (m, 7H), 3.27 (q, J=6.6 Hz, 2H), 2.96 (q, J=5.5 Hz, 2H), 2.34 (t, J=6.5 Hz, 2H), 1.98 (t, J=6.5 Hz, 2H). $^{13}$C-NMR (500 MHz, DMSO-d6): δ 116.96, 69.55, 69.29, 66.73, 66.61, 56.38, 38.57, 36.03, 35.63, 28.58. ESI-MS (m/z) for $C_{25}H_{31}ClFN_5O_5$ (exact mass 535.20): [M+H]$^+$ calc. 536.2, obs. 536.3.

Figure 14:
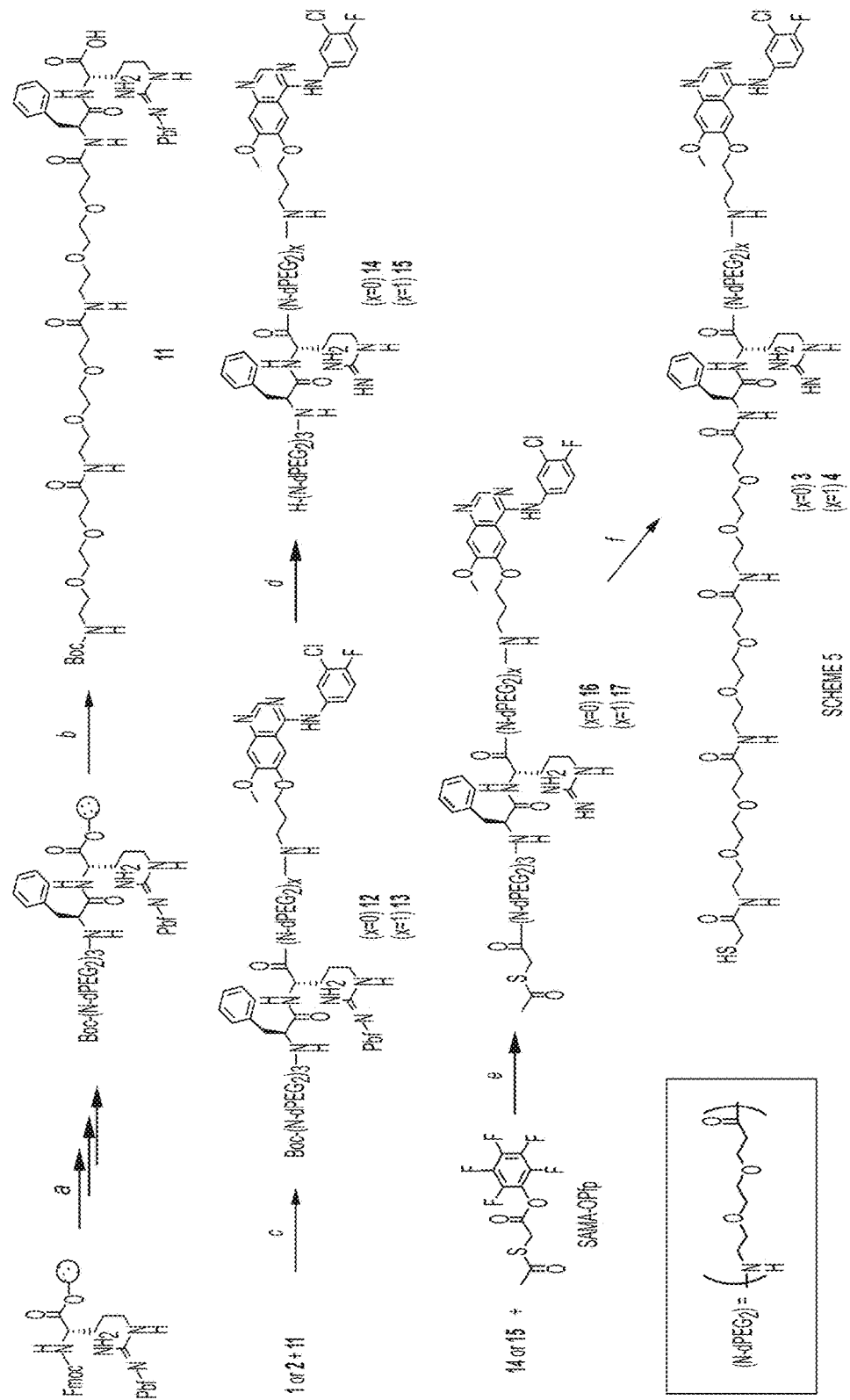
FIG. 14 shows Scheme 5, which illustrates a synthesis process of Phe-Arg-APdMG 3 and Phe-Arg-dPEG$_2$APdMG 4.

Preparation of Boc-N-amino-(dPEG$_2$)$_3$-Phe-Arg (PbJ)-OH (11, in FIG. 14 (Scheme 5))

Chlorotrityl resin (100 mg, 0.1 mmol, 1 mmol/g) was transferred into a fritted syringe reaction vessel and suspended in 2 mL anhydrous DCM for 10 min. The solvent was dispensed, and a solution of DIEA in anhydrous DCM followed by a solution of Fmoc-Arg(Pbf)-OH (97.5 mg, 1.5 eq) in anhydrous DCM were drawn into the syringe; and agitated for 40 min. The solution was dispensed and the resin washed for 2 min, 2× with DCM, then 2× with DMF. Standard solid phase peptide synthesis procedures were the carried out to obtain the final peptide. In short Fmoc deprotections were accomplished by washing the resin 2× using 30% piperidine/DMF (1 mL) for 10 min. This was followed by DMF (1 mL) washes, 4× for 2 min each. Coupling reactions were carried out at room temp using a 3 eq excess of protected amino acid (in 2 mL DMF), 9 eq excess of DIEA (120 mg, 0.9 mmol, 160 μL, in 1 mL DMF), 3 eq excess of HATU (mmol, mg, μL, in 2 mL DMF), added to the syringe in that order, and shaken for 1 hr. This was followed by DMF (1 mL) washes, 4× for 2 min each. Fmoc-Phe (116 mg) was added, followed by three residues of Fmoc-N-dPEG$_2$-OH (120 mg). After completion of the sequence, final Fmoc deprotection and washes, BOC anhydride (mmol, mg) and DIEA (mmol, mg, μL) in 2 mL of DMF were used to cap the N-terminal amine. The peptide-resin was washed with DMF (1 mL, 2 min, 2×), then DCM (1 mL, 2 min, 4×). The protected peptide product was then cleaved off of the resin by adding 50% HFIP in DCM (2 mL) to the syringe and shaking for 1 hr at room temp. The crude peptide was then purified by reversed phase HPLC. ESI-MS (m/z) for $C_{54}H_{86}N_8O_{17}S$ (exact mass 1150.56): [M+H]$^+$ calc. 1151.6, obs. 1151.7.

Preparation of Boc-N-amido-(dPEG$_2$)$_3$-Phe-Arg (Pbf)-APdMG (12, in FIG. 14 (Scheme 5))

A solution containing compound 11 (23 mg, 0.02 mmol, 1 eq) and APdMG 1 (9 mg, 0.024 mmol, 1.2 eq) in DMF (1 mL) was prepared. To this DIEA (10 mg, 0.08 mmol, 14 μL, 4 eq) was added followed by HATU (9 mg, 0.024 mmol, 1.2 eq). The reaction was monitored by HPLC, and completed within 30 minutes. The solvent was removed in vacuo, then resuspended in DCM. The DCM solution was washed with water 4×, then evaporated leaving a tan oil. ESI-MS (m/z)

Preparation of Boc-N-amido-(dPEG$_2$)$_3$-Phe-Arg (Pbf)-dPEG$_2$APdMG (13, in FIG. 14 (Scheme 5))

A solution containing compound 11 (30 mg, 0.026 mmol, 1 eq) and dPEG$_2$APdMG 2 (18 mg, 0.034 mmol, 1.3 eq) in DMF (1 mL) was prepared. To this DIEA (14 mg, 0.1 mmol, 18 µL, 4 eq) was added followed by HATU (13 mg, 0.034 mmol, 1.3 eq). The reaction was monitored by HPLC, and completed within 30 minutes. The solvent was removed in vacuo, then resuspended in DCM. The DCM solution was washed with water 4×, then evaporated leaving a tan oil. ESI-MS (m/z) for C$_{79}$H$_{115}$ClFN$_{13}$O$_{21}$S (exact mass 1667.77): [M+2H]$^{2+}$ calc. 834.9, obs. 834.7.

Preparation of H$_2$N-(dPEG$_2$)$_3$-Phe-Arg-APdMG (14, in Scheme 6)

TFA/water (9:1, 1 mL) was added compound 12 (~0.02 mmol from previous step) and left at room temperature for 1 hour. The reaction was evaporated then dissolved in ACN/water, frozen and lyophilized leaving a tan solid. The crude material was purified by reversed phase HPLC. The final product was left as a white solid (14 mg). ESI-MS (m/z) for C$_{54}$H$_{78}$ClFN$_{12}$O$_{13}$ (exact mass 1156.55): [M+H]$^+$ calc. 1157.6, obs. 1157.8; [M+2H]$^{2+}$ calc. 579.3, obs. 579.1.

Preparation of H$_2$N-(dPEG$_2$)$_3$-Phe-Arg-(dPEG$_2$)-APdMG (15, in FIG. 14 (Scheme 5))

TFA/water (9:1, 1 mL) was added compound 13 (~0.026 mmol from previous step) and left at room temp for 1 hour. The reaction was evaporated then dissolved in ACN/water, frozen and lyophilized leaving a tan solid. The crude material was purified by reversed phase HPLC. The final product was left as a white solid (24 mg). ESI-MS (m/z) for C$_{61}$H$_{91}$ClFN$_{13}$O$_{16}$ (exact mass 1315.64): [M+H]$^+$ calc. 1316.7, obs. 1316.5; [M+2H]$^{2+}$ calc. 658.6, obs. 658.5.

Preparation of S-Acetyl-mercaptoacetamido-(dPEG$_2$)$_3$-Phe-Arg-APdMG (16, in FIG. 14 (Scheme 5))

A solution containing compound 14 (5 mg, 0.004 mmol, 1 eq) and DIEA (1.5 mg, 0.012 mmol, 2 µL, 3 eq) in DMF (200 µL) was prepared. SAMA-OPfp (2 mg, 0.006 mmol, 1.5 eq) in DMF (100 µL) was then added to the solution, and allowed to react for 1 hour. The solvent was removed in vacuo then purified by reversed phase HPLC. 3 mg of a white solid was recovered. ESI-MS (m/z) for C$_{61}$H$_{91}$ClFN$_{13}$O$_{16}$ (exact mass 1315.64): [M+H]$^+$ calc. 1316.7, obs. 1316.5; [M+2H]$^{2+}$ calc. 658.6, obs. 658.5.

Preparation of S-Acetyl-mercaptoacetamido-(dPEG$_2$)$_3$-Phe-Arg-dPEG$_2$APdMG (17, in FIG. 14 (Scheme 5))

A solution containing compound 15 (5 mg, 0.004 mmol, 1 eq) and DIEA (1.5 mg, 0.012 mmol, 2 µL, 3 eq) in DMF (200 µL) was prepared. SAMA-OPfp (2 mg, 0.006 mmol, 1.5 eq) in DMF (100 µL) was then added to the solution, and allowed to react for 1 hour. The solvent was removed in vacuo then purified by reversed phase HPLC. 3 mg of a white solid was recovered. ESI-MS (m/z) for C$_{65}$H$_{95}$ClFN$_{13}$O$_{18}$S (exact mass 1431.63): [M+2H]$^{2+}$ calc. 716.8, obs. 716.7.

Preparation of Mercaptoacetamido-(dPEG$_2$)$_3$-Phe-Arg-APdMG, Phe-Arg-APdMG (3, in FIG. 1B and FIG. 14 (Scheme 5))

This step was performed immediately prior to use. 1 mg of compound 16 was dissolved in 100 µL of water/MeOH (1:1), to which 2 µL of 1 N NaOH was added. After 15 minutes, 2 uL of 1 M HCl was added to neutralize. The solution was directly used. ESI-MS (m/z) for C$_{56}$H$_{80}$ClFN$_{12}$O$_{14}$S (exact mass 1230.53): [M+H]$^+$ calc. 1231.5, obs. 1231.4; [M+2H]$^{2+}$ calc. 616.3, obs. 616.3.

Preparation of Mercaptoacetamido-(dPEG$_2$)$_3$-Phe-Arg-dPEG$_2$APdMG, Phe-Arg-dPEG$_2$APdMG (4, in FIG. 1C and FIG. 14 (Scheme 5))

This step was performed immediately prior to use. 1 mg of compound 17 was dissolved in 100 µL of water/MeOH (1:1), to which 2 µL of 1 N NaOH was added. After 15 minutes, 2 uL of 1 M HCl was added to neutralize. The solution was directly used. ESI-MS (m/z) for C$_{63}$H$_{93}$ClFN$_{13}$O$_{17}$S (exact mass 1389.62): [M+H]$^+$ calc. 1390.6, obs. 1390.5; [M+2H]$^{2+}$ calc. 695.8, obs. 695.7.

Figure 15:
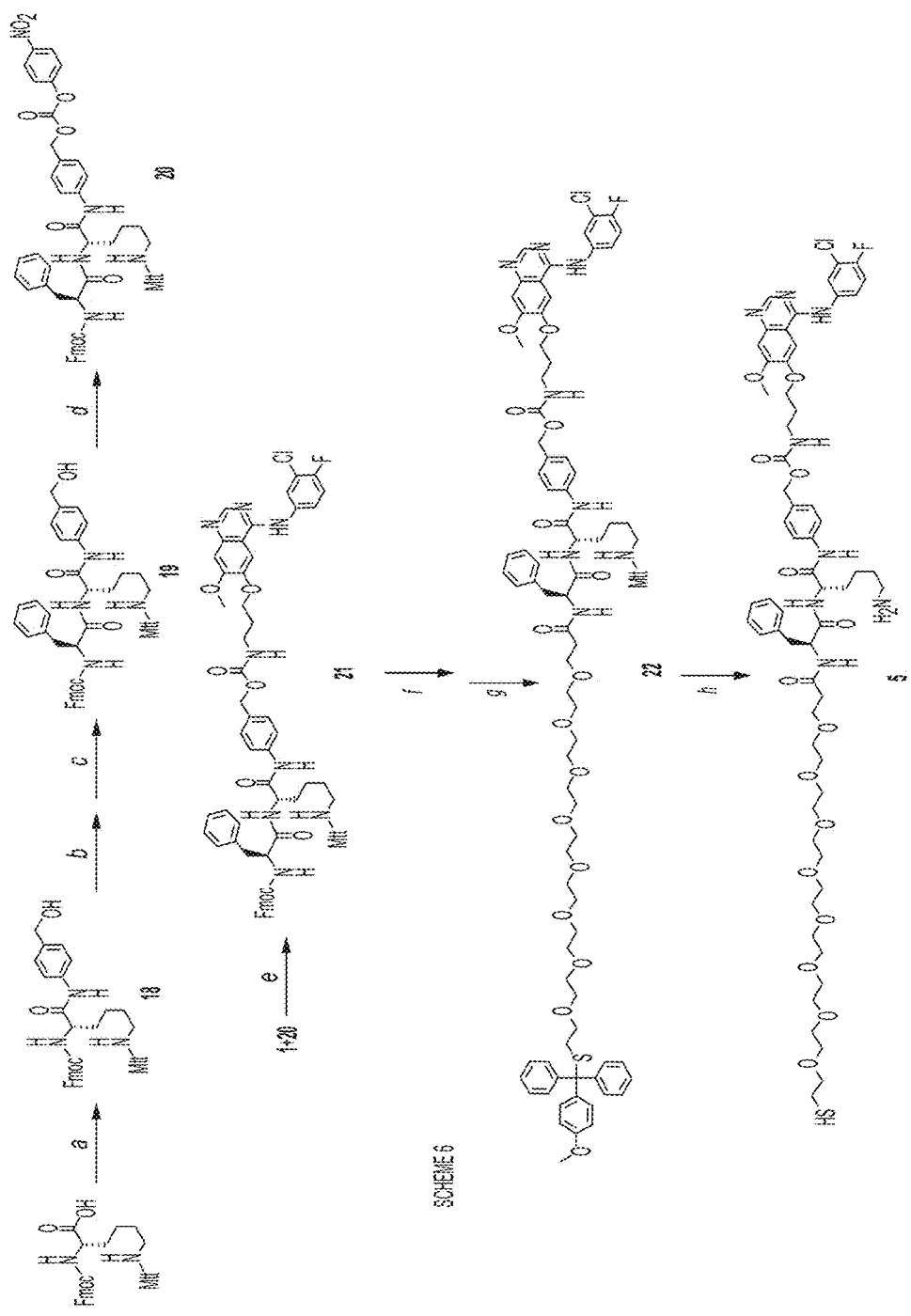
FIG. 15 shows Scheme 6, which illustrates a synthesis process of Phe-Lys-PABC-APdMG (5).
Figure 16C:
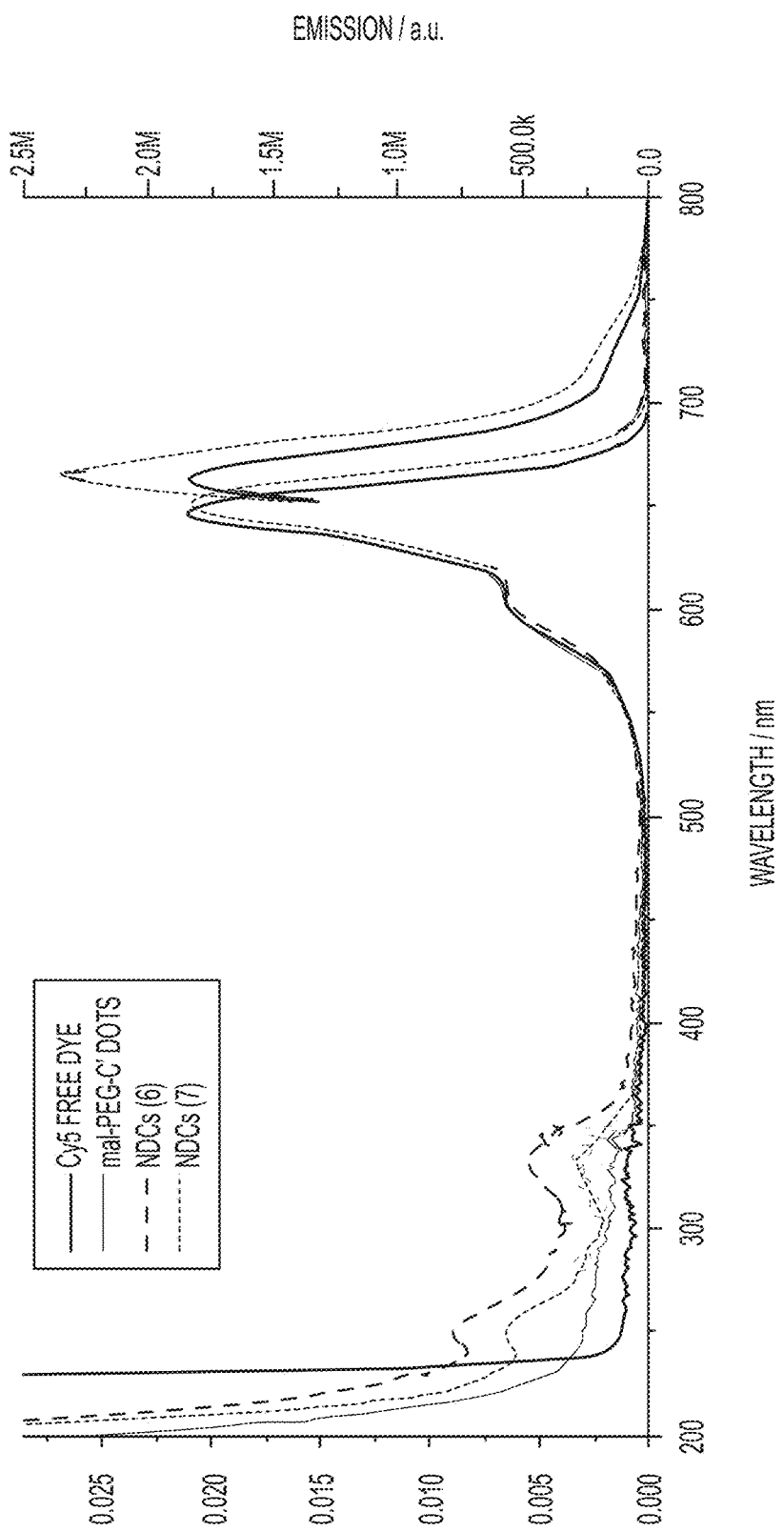
Figure 16D:
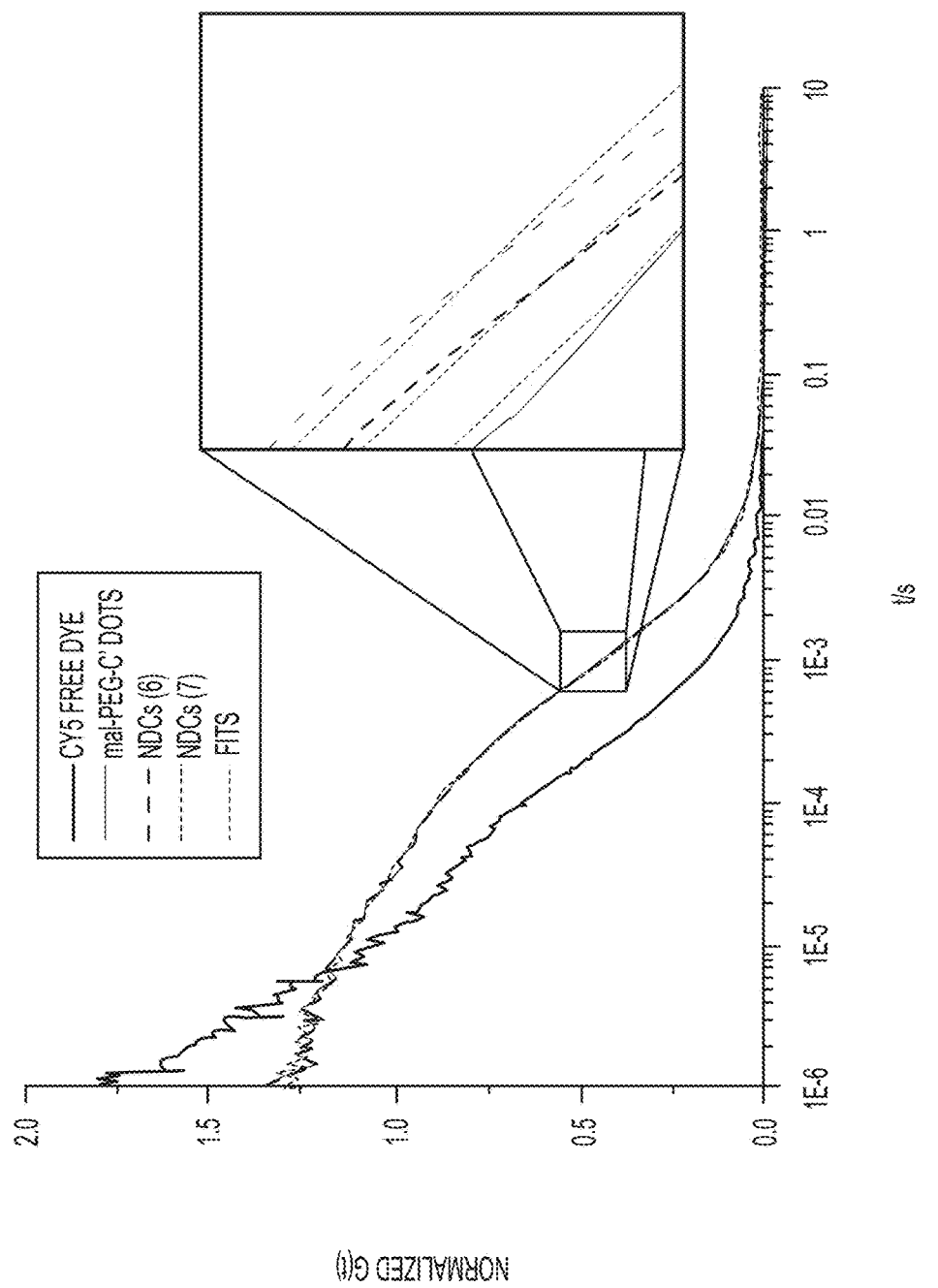

Preparation of Fmoc-Lys(Mtt)-PABOH (18, in FIG. 15 (Scheme 6))

A solution of Fmoc-Lys(Mtt)-OH (748 mg, 1.2 mmol, 1 eq) and para-amino benzyl alcohol (300 mg, 2.4 mmol, 2 eq) in DMF (5 mL) was prepared. DIEA (465 mg, 3.6 mmol, 630 µL, 3 eq) was added followed by a solution of HATU (502 mg, 1.3 mmol, 1.1 eq) in DMF (2 mL). The reaction was complete within 30 minutes and as determined by HPLC/LCMS. The solvent was partially removed in vacuo, and extracted with ethyl acetate/water. The ethyl acetate layer was washed 4× with water, then evaporated leading to an orange solid. The crude material was purified on a 40 g RediSep Rf normal phase cartridge using a linear gradient of hexane and ethyl acetate. The final product was isolated as a white solid (850 mg, 97% yield).

$^1$H-NMR (500 MHz, CDCl$_3$): δ 7.96 (s, 1H), 7.73 (d, J=7.9 Hz, 2H), 7.54 (d, J=7.5 Hz, 2H), 7.47-7.41 (m, 6H), 7.39-7.20 (m, 12H), 7.18-7.11 (m, 2H), 7.05 (d, J=7.9 Hz, 2H), 5.29 (s, 1H), 4.63 (s, 1H), 4.44 (d, J=6.4 Hz, 2H), 2.28 (s, 3H), 2.11 (t, J=6.9 Hz, 2H), 1.88 (s, 1H), 1.58 (s, 5H), 1.51 (s, 1H), 1.38 (s, 2H). $^{13}$C-NMR (500 MHz, CDCl$_3$): δ 146.36, 143.22, 141.32, 135.70, 128.57, 128.52, 128.49, 127.79, 127.74, 127.12, 126.14, 124.92, 120.16, 120.02, 77.27, 77.02, 76.76, 70.62, 64.92, 60.41, 47.16, 43.30, 30.57, 23.43, 21.07, 20.93, 14.21, 0.01. ESI-MS (m/z) for C$_{48}$H$_{47}$N$_3$O$_4$ (exact mass 729.36): [M+H]$^+$ calc. 730.4, obs. 730.2.

Preparation of Fmoc-Phe-Lys(Mtt)-PABOH (19, in FIG. 15, (Scheme 6))

The Fmoc group was removed from Fmoc-Lys(Mtt)-PABOH 18 (425 mg, 0.6 mmol, 1 eq) using 9 mL of 30% piperidine in DMF for 10 minutes. The solvent was removed in vacuo, and the resulting oil was resuspended in 10 mL DMF A solution of Fmoc-Lys(Mtt)-OH (748 mg, 1.2 mmol, 1 eq) and para-amino benzyl alcohol (300 mg, 2.4 mmol, 2 eq) in DMF (5 mL) was prepared. DIEA (465 mg, 3.6 mmol, 630 µL, 3 eq) was added followed by a solution of HATU (502 mg, 1.3 mmol, 1.1 eq) in DMF (2 mL). The reaction was complete within 30 minutes and as determined by HPLC/LCMS. The solvent was partially removed in vacuo, and extracted with ethyl acetate/water. The ethyl acetate layer was washed 4× with water, then evaporated leading to an orange solid. The crude material was purified on a 40 g RediSep Rf normal phase cartridge using a linear gradient of hexane and ethyl acetate. The final product was isolated as a white solid (850 mg, 97% yield).

$^1$H-NMR (500 MHz, CDCl$_3$) δ 8.20 (s, 1H), 7.73 (d, J=7.6 Hz, 2H), 7.50 (s, 2H), 7.48-7.34 (m, 8H), 7.34-7.20 (m, 11H), 7.20-7.07 (m, 7H), 7.04 (d, J=8.1 Hz, 2H), 6.28 (s, 1H), 5.22 (s, 1H), 4.62 (s, 2H), 4.43 (dd, J=10.7, 6.7 Hz, 1H), 4.32 (d, J=11.5 Hz, 1H), 3.05 (s, 2H), 2.27 (s, 3H), 2.11-2.02 (m, 2H), 1.89 (s, 1H), 1.46 (d, J=6.3 Hz, 1H), 1.26 (s, 2H). $^{13}$C-NMR (500 MHz, CDCl$_3$) δ 146.35, 141.31, 136.97, 135.70, 129.10, 128.93, 128.57, 128.50, 127.82, 127.74, 127.71, 127.39, 127.12, 126.14, 124.91, 124.84, 120.10, 120.04, 77.28, 77.23, 77.02, 76.77, 70.60, 67.15, 64.96, 54.06, 47.08, 43.35, 31.30, 30.60, 23.52, 20.93. ESI-MS (m/z) for $C_{57}H_{56}N_4O_5$ (exact mass 876.43): [M+H]$^+$ calc. 877.4, obs. 877.3.

Preparation of Fmoc-Phe-Lys(Mtt)-PABC-APdMG (21, in FIG. 15 (Scheme 6))

Compound 19 (420 mg, 0.5 mmol, 1 eq) was dissolved in anhydrous DCM (20 mL). Pyridine (216 mg, 2.7 mmol, 5.4 eq) was added, followed by a solution of 4-nitrophenyl chloroformate (180 mg, 0.9 mmol, 1.8 eq) in anhydrous DCM. The reaction proceeded for 2 hours at room temperature, then checked by HPLC and TLC. The solvent was removed in vacuo then purified by on a 24 g RediSep Rf normal phase cartridge using a linear gradient of hexane and ethyl acetate. The product Fmoc-Phe-Lys(Mtt)-PABC-pNP (20), was isolated as a yellow solid (360 mg, 70% yield). Fmoc-Phe-Lys(Mtt)-PABC-pNP (50 mg, 0.05 mmol, 1 eq) was dissolved in anhydrous DCM (3 mL). A solution of APdMG 1 (25 mg, 0.05 mmol, TFA salt, 1 eq) with DIEA (65 mg, 0.5 mmol, 90 µL, 10 eq) in anhydrous DCM was then added to Fmoc-Phe-Lys(Mtt)-PABC-pNP. The reaction proceeded at room temperature for 4 hours, then checked by HPLC and TLC. The solvent was removed in vacuo, and the crude material was purified on a 4 g RediSep Rf normal phase cartridge with a linear gradient of hexane and ethyl acetate. The final product was isolated as a yellow solid (38 mg, 60% yield). ESI-MS (m/z) for $C_{76}H_{72}ClFN_8O_8$ (exact mass 1278.51): [M+H]$^+$ calc. 1279.5, obs. 1279.4; [M+2H]$^{2+}$ calc. 640.3, obs. 640.3.

Preparation of Mmt-S-dPEG$_8$-Phe-Lys(Mtt)-pABC-dMG (22, in FIG. 15 (Scheme 6))

18 mg of compound 21 (0.014 mmol, 1 eq) was deprotected with 2 mL of 30% piperidine in DMF. After 5 minutes the reaction was confirmed complete by HPLC/LCMS, and the solvent was removed in vacuo. The resulting oil was dissolved in DMF (0.5 mL), to which Mmt-S-dPEG$_8$-COOH (13 mg, 0.017 mmol, 1.2 eq) and DIEA (9 mg, 0.070 mmol, 13 µL, 5 eq) were added. A solution of HATU (6 mg, 0.014 mmol, 1.2 eq) in DMF (200 µL) was prepared and added to the reaction. After 1 hr, the reaction was deemed complete by HPLC/LCMS, and solvent was removed in vacuo. The remaining oil was flash purified on a 4 g RediSep Rf normal phase cartridge using a linear gradient of DCM to 10% MeOH in DCM. The final product was isolated as a white solid (23 mg, 92% yield). ESI-MS (m/z) for $C_{100}H_{114}ClFN_8O_{16}S$ (exact mass 1768.77): [M+2H]$^{2+}$ calc. 885.9, obs. 886.0.

Preparation of HS-dPEG$_8$-Phe-Lys-PABC-aminopropyl-dMG (5, in FIG. 15 (Scheme 6))

10 mg of compound 22 (5.6 µmol) was treated with 2 mL of 0.5% TFA/5% TIS in DCM for 2 hrs, then checked by HPLC/LCMS to confirm complete deprotection. The solution was removed in vacuo, and then washed with cold ether, 3×. The white solid was dissolved in water/acetonitrile (1:1), frozen and lyophilized. The resulting white solid was used without further purification (6 mg, 86% yield). ESI-MS (m/z) for $C_{60}H_{82}ClFN_8O_{15}S$ (exact mass 1240.53): [M+H]$^+$ calc. 1241.5, obs. 1241.6; [M+2H]$^{2+}$ calc. 621.3, obs. 621.3.

Preparation of the C'Dot-(Cy5)-PEG-Maleimide

A maleimide and NHS ester functionalized polyethylene glycol (mal-dPEG$_{12}$-NHS) was conjugated with aminosilane (APTES) in DMSO (molar ratio mal-PEG-NHS:APTES:DMSO 1:0.9:60). The reaction mixture was left under nitrogen at room temperature for 48 hours to generate silane functionalized mal-dPEG (mal-dPEG-APTES). A maleimide functionalized Cy5 (mal-Cy5) was reacted with a thiol-silane (MPTMS) in DMSO (molar ratio Cy5:MPTMS:DMOS 1:25:1150). The reaction was left under nitrogen at room temperature for 24 hours to generate a silane functionalized Cy5 (Cy5-MPTMS). TMOS and Cy5-MPTMS were then titrated into an ammonia hydroxide solution (~pH 8) (molar ratio TMOS:Cy5:NH3:H2O 1:0.001:0.44:1215). The solution was stirred at 600 rpm at room temperature for 24 hours to form homogeneous Cy5 encapsulated silica nanoparticles. The mal-dPEG-APTES and silane functionalized polyethylene glycol (PEG-silane, MW around 500, Gelest) were then added into the synthesis solution to PEGylate and surface-functionalize the particles (PEG-silane:TMOS:mal-PEG-APTES 1:2.3:0.006). The solution was stirred at 600 rpm at room temperature for 24 hours followed by incubation at 80° C. for another 24 hours without stirring. The solution was dialyzed in 2000 mL with deionized water for two days (10 k MWCO), filtered with 200 nm syringe filters, and finally chromatographically purified (Superdex 200) resulting in the desired mal-C'dots.

Preparation of C'Dot-(Cy5)-PEG-Phe-Arg-dPEG$_2$-Gly-D-Tyr-APdMG

The same overall synthetic strategy used to obtain compound 6 was used. The linker-drug construct Phe-Arg-dPEG$_2$-Gly-D-Tyr-APdMG (23) was synthesized. (ESI-MS (m/z) for $C_{74}H_{105}ClFN_{15}O_{20}S$ (exact mass 1609.71): [M+2H]$^{2+}$ calc. 805.9, obs. 805.6). This construct was attached to C'dot-(Cy5)-PEG-mal as described for NDCs 6 and 7.

Preparation of C'Dot-(Cy5)-PEG-Phe-Lys-PABC-Gly-D-Tyr-APdMG

The same overall synthetic strategy used to obtain compound 7 was used. The linker-drug construct Phe-Lys-PABC-Gly-D-Tyr-APdMG (24) was synthesized. (ESI-MS (m/z) for $C_{71}H_{94}ClFN_{10}O_{18}S$ (exact mass 1460.61): [M+H]$^+$ calc. 1461.6, obs. 1461.3; [M+2H]$^{2+}$ calc. 731.3, obs. 731.5). This construct was attached to C'dot-(Cy5)-PEG-mal as described for NDCs 6 and 7.

Preparation of Radioiodination of C'Dot-(Cy5)-PEG-Phe-Arg-dPEG$_2$-Gly-D-Tyr-aminopropyl-APdMG Radioiodination was carried out on C'dot-(Cy5)-PEG-Phe-Arg-dPEG$_2$-Gly-D-Tyr-APdMG using Iodogen protocols. Iodination reactions were purified on a PD10 column, then analyzed by GPC (Superdex).

What is claimed is:

1. A nanoparticle drug conjugate (NDC) comprising:
a non-mesoporous nanoparticle, wherein the non-mesoporous nanoparticle comprises a silica-based core and a silica shell surrounding a least a portion of the core;
an enzyme sensitive linker moiety; and
a drug moiety,
wherein the non-mesoporous nanoparticle comprises silica,
wherein the NDC has a diameter less than 25 nm, and
wherein the drug moiety and enzyme sensitive linker moiety form a cleavable linker-drug construct that facilitates enzyme catalyzed drug release.

2. The NDC of claim 1, wherein the enzyme sensitive linker moiety comprises one or more amino acids.

3. The NDC of claim 1, wherein the enzyme sensitive linker moiety comprises (Amino-(spacer)$_x$)$_y$-peptide or (spacer)$_z$-peptide, wherein the spacer has from 2 to 50 atoms,
wherein x is an integer from 1 to 5,
wherein y is an integer from 1 to 5,
wherein z is an integer from 5 to 15, and
wherein the enzyme sensitive linker moiety comprises a degradable moiety between the enzyme sensitive linker moiety and the drug moiety.

4. The NDC of claim 1, wherein the enzyme sensitive linker moiety comprises a spacer between a peptide and the drug moiety.

5. The NDC of claim 1, comprising an imaging agent.

6. The NDC of claim 5, wherein the imaging agent comprises a radiolabel.

7. The NDC of claim 1, wherein the enzyme sensitive linker moiety is capable of undergoing hydrolysis at a C-terminal end upon protease binding, thereby releasing the drug moiety from the non-mesoporous nanoparticle.

8. The NDC of claim 1, wherein the drug moiety comprises a receptor tyrosine kinase (RTK) inhibitor.

9. The NDC of claim 1, further comprising from 1 to 20 targeting moieties, wherein the targeting moieties bind to receptors on tumor cells.

10. The NDC of claim 9, wherein the NDC is a theranostic.

11. The NDC of claim 1, wherein the non-mesoporous nanoparticle is coated with an organic polymer, wherein the cleavable linker-drug construct is covalently linked to the polymer-coated non-mesoporous nanoparticle.

12. The NDC of claim 5, wherein the imaging agent comprises a fluorescent compound.

13. The NDC of claim 12, wherein the fluorescent compound is Cy5.5.

14. The NDC of claim 6, wherein the drug moiety is attached to the radiolabel.

15. The NDC of claim 3, wherein the enzyme sensitive linker moiety comprises one or more amino acids, wherein
the one or more amino acids include a peptide or polypeptide, and include 1 to 10 amino acids,
the (Amino-(spacer)$_x$)$_y$-peptide or (spacer)$_z$-peptide is a dipeptide, the dipeptide being one of phenylalanine-arginine (Phe-Arg) or phenylalanine-lysine (Phe-Lys),
the spacer is PEG, and
the degradable moiety is an amide bond, the degradable moiety allowing cleavage the drug moiety in the presence of a protease.

16. The NDC of claim 4, wherein
the spacer comprises a member selected from the group consisting of polyethylene glycol (PEG), PEG$_2$, and para-aminobenzyloxy carbamate (PABC).

17. The NDC of claim 7, wherein the protease is serine protease including trypsin, or cysteine protease including cathepsin B.

18. The NDC of claim 8, wherein the receptor tyrosine kinase (RTK) inhibitor is dasatinib or gefitinib, including analogs thereof, or pharmaceutical or therapeutic equivalents thereof, modified to provide attachment to the enzyme sensitive linker moiety without perturbing underlying chemical structure of an active binding site of the drug moiety.

19. The NDC of claim 9, wherein the targeting moieties include cyclic arginylglycylaspartic acid (cRGD).

20. The NDC of claim 11, wherein
the drug moiety includes a dasatinib or gefitinib, and analogs thereof,
the organic polymer comprises at least one bifunctionalized maleimide silyl-polyethylene glycol group attached to at least one linker-drug construct,
the cleavable linker-drug construct is formed via a protease, the linker-drug construct being linked to the non-mesoporous nanoparticle via the linker moiety, and
the average drug moiety to non-mesoporous nanoparticle ratio ranges from 1 to 20.

21. The NDC of claim 5, wherein the non-mesoporous nanoparticle comprises a metal and wherein the imaging agent comprises the metal.

22. The NDC of claim 21, wherein the metal comprises gold.

23. The NDC of claim 21, wherein the metal comprises a transition metal complex.

24. The NDC of claim 21, wherein the non-mesoporous nanoparticle has a core comprising the metal.

* * * * *

UNITED STATES PATENT AND TRADEMARK OFFICE
CERTIFICATE OF CORRECTION

PATENT NO. : 10,485,881 B2
APPLICATION NO. : 16/137709
DATED : November 26, 2019
INVENTOR(S) : Michelle S. Bradbury et al.

Page 1 of 1

It is certified that error appears in the above-identified patent and that said Letters Patent is hereby corrected as shown below:

In the Claims

In Claim 1, Column 25, Line 16, please delete "a least" and insert -- at least --

Signed and Sealed this
Twenty-eighth Day of January, 2020

Andrei Iancu
*Director of the United States Patent and Trademark Office*